United States Patent
Vogt et al.

(10) Patent No.: US 11,701,156 B2
(45) Date of Patent: Jul. 18, 2023

(54) BONE CEMENT APPLICATOR WITH CLAMPABLE DELIVERY PLUNGER

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 490 days.

(21) Appl. No.: 16/793,150

(22) Filed: Feb. 18, 2020

(65) Prior Publication Data
US 2020/0261133 A1 Aug. 20, 2020

(30) Foreign Application Priority Data

Feb. 18, 2019 (DE) ...................... 10 2019 104 020.5

(51) Int. Cl.
*A61B 17/88* (2006.01)
*A61L 24/06* (2006.01)
(Continued)

(52) U.S. Cl.
CPC .......... *A61B 17/8822* (2013.01); *A61L 24/06* (2013.01); *B01F 23/511* (2022.01);
(Continued)

(58) Field of Classification Search
CPC . A61B 17/88; A61B 17/8825; A61B 17/8833; A61B 2017/8838; B01F 35/754251; B01F 35/7174; B01F 35/7161
See application file for complete search history.

(56) References Cited

U.S. PATENT DOCUMENTS 3,475,010 A * 10/1969 Moline ............... B01F 35/7137
222/136
4,671,263 A   6/1987 Draenert
(Continued)

FOREIGN PATENT DOCUMENTS

DE   2921565   12/1980
DE   3640279   6/1987
(Continued)

OTHER PUBLICATIONS

Charnley, J., "Anchorage of the Femoral Head Prosthesis of the Shaft of the Femur," The Journal of Bone and Joint Surgery, 42 B, No. 1, pp. 28-30 (Feb. 1960).
(Continued)

*Primary Examiner* — Anu Ramana
(74) *Attorney, Agent, or Firm* — Dicke, Billig & Czaja, PLLC

(57) ABSTRACT

One aspect relates to a bone cement applicator having a cartridge with an interior, a cartridge head with a delivery opening, a mixing member which is movable in the interior with a mixing rod. A delivery plunger is arranged in the cartridge and is mounted in the interior and is pressable in the direction of the delivery opening. The delivery plunger rests with an outer cylindrical circumferential surface against an inner wall of the cartridge. A clamping element is arranged on the inner wall of the cartridge in the region of a back side of the interior. The clamping element projects out of the inner wall of the cartridge. The cylindrical circumferential surface of the delivery plunger is resiliently deformable by the clamping element in the direction of a central cylinder axis, such that the delivery plunger is clampable in place with the at least one clamping element on the back side of the cartridge.

20 Claims, 13 Drawing Sheets

(51) Int. Cl.
*B01F 23/50* (2022.01)
*B01F 35/75* (2022.01)
*A61B 17/00* (2006.01)
*B01F 101/20* (2022.01)

(52) U.S. Cl.
CPC ............. *B01F 35/754251* (2022.01); *A61B 2017/00955* (2013.01); *A61B 2017/8838* (2013.01); *B01F 2101/20* (2022.01)

(56) References Cited

U.S. PATENT DOCUMENTS

| | | | |
|---|---|---|---|
| 4,758,096 A | 7/1988 | Gunnarsson | |
| 4,776,704 A * | 10/1988 | Kopunek | B01F 33/5011 |
| | | | 222/386 |
| 4,973,168 A | 11/1990 | Chan | |
| 5,100,241 A | 3/1992 | Chan | |
| 5,114,240 A | 5/1992 | Kindt-Larsen et al. | |
| 5,252,301 A | 10/1993 | Nilson et al. | |
| 5,344,232 A | 9/1994 | Nelson et al. | |
| 5,551,778 A | 9/1996 | Hauke et al. | |
| 5,558,136 A | 9/1996 | Orrico | |
| 5,586,821 A | 12/1996 | Bonitati et al. | |
| 5,588,745 A | 12/1996 | Tanaka et al. | |
| 5,624,184 A | 4/1997 | Chan | |
| 5,779,356 A | 7/1998 | Chan | |
| 5,997,544 A | 12/1999 | Nies et al. | |
| 6,033,105 A | 3/2000 | Barker et al. | |
| 6,120,174 A | 9/2000 | Hoag et al. | |
| 6,709,149 B1 | 3/2004 | Tepic | |
| 6,755,563 B2 | 6/2004 | Wahlig et al. | |
| 7,073,936 B1 | 7/2006 | Jonsson | |
| 7,306,361 B2 * | 12/2007 | Coffeen | B01F 31/441 |
| | | | 366/195 |
| 7,959,349 B2 | 6/2011 | Sattig et al. | |
| 8,128,276 B2 | 3/2012 | Axelsson et al. | |
| 8,757,866 B2 | 6/2014 | Vogt et al. | |
| 9,095,871 B2 * | 8/2015 | Vogt | B05C 17/00596 |
| 9,694,514 B2 | 7/2017 | Vogt | |
| 9,827,030 B2 * | 11/2017 | Vogt | B05C 17/00553 |
| 10,143,979 B2 | 12/2018 | Vogt et al. | |
| 10,307,508 B2 | 6/2019 | Vogt | |
| 10,966,769 B2 * | 4/2021 | Larsson | A61B 17/8825 |
| 2016/0015854 A1 * | 1/2016 | Vogt | B29B 7/24 |
| | | | 366/139 |
| 2018/0132917 A1 | 5/2018 | Vogt et al. | |
| 2018/0132919 A1 | 5/2018 | Vogt et al. | |
| 2018/0132979 A1 | 5/2018 | Vogt et al. | |
| 2018/0256233 A1 | 9/2018 | Vogt et al. | |
| 2018/0289406 A1 | 10/2018 | Vogt et al. | |
| 2018/0310974 A1 | 11/2018 | Vogt et al. | |
| 2018/0333176 A1 | 11/2018 | Vogt et al. | |

FOREIGN PATENT DOCUMENTS

| | | |
|---|---|---|
| DE | 69812726 | 2/2004 |
| DE | 102007026034 | 12/2008 |
| DE | 102009031178 | 9/2010 |
| DE | 102012024710 | 5/2014 |
| EP | 0397589 | 11/1990 |
| EP | 0692229 | 1/1996 |
| EP | 0796653 | 9/1997 |
| EP | 1005901 | 6/2000 |
| EP | 1016452 | 7/2000 |
| EP | 1020167 | 7/2000 |
| EP | 1886647 | 2/2008 |
| EP | 2 974 681 | 1/2016 |
| EP | 3 231 505 | 10/2017 |
| WO | 90/13264 | 11/1990 |
| WO | 94/26403 | 11/1994 |
| WO | 99/67015 | 12/1999 |
| WO | 2004/100771 | 6/2000 |
| WO | 01/85070 | 11/2001 |

OTHER PUBLICATIONS

Kühn, Klaus-Dieter, "Bone Cements," Springer-Verlag, pp. 9 (2000).

* cited by examiner

BONE CEMENT APPLICATOR WITH CLAMPABLE DELIVERY PLUNGER

CROSS-REFERENCE TO RELATED APPLICATION

This Utility patent application claims priority to German Application No. 10 2019 104 020.5 filed on Feb. 18, 2019, which is incorporated herein by reference.

TECHNICAL FIELD

One embodiment relates to a bone cement applicator for producing a bone cement from a monomer liquid and a cement powder as parent components of the bone cement paste and for delivering the mixed bone cement paste.

One embodiment also relates to a method for producing a bone cement paste, in particular a paste-like polymethyl methacrylate bone cement paste, using such a bone cement applicator.

BACKGROUND

Polymethyl methacrylate (PMMA) bone cements date back to the fundamental work of Sir Chamley (Charnley, J.: Anchorage of the femoral head prosthesis of the shaft of the femur. J. Bone Joint Surg. 42 (1960) 28-30). Conventional polymethyl methacrylate bone cements (PMMA bone cements) are composed of a powdery component and a liquid monomer component (K.-D. Kuhn: Knochenzemente fir die Endoprothetik: Ein aktueller Vergleich der physikalischen und chemischen Eigenschaften handelsüblicher PMMA-Zemente [Bone cements for endoprosthetics: A current comparison of the physical and chemical properties of commercial PMMA cements], Springer-Verlag Berlin Heidelberg New York, 2001). The monomer component generally contains the monomer methyl methacrylate and an activator (N,N-dimethyl-p-toluidine) dissolved therein. The powder component, also referred to as cement powder or bone cement powder, has one or more polymers which are produced on the basis of methyl methacrylate and comonomers, such as styrene, methyl acrylate or similar monomers through polymerization, preferably suspension polymerization, a radiopaque substance and the initiator dibenzoyl peroxide. When the powder component is mixed with the monomer component, a plastically deformable paste, the actual bone cement or bone cement paste, is produced as a result of the expansion of the polymers of the powder component in the methyl methacrylate. When the powder component is mixed with the monomer component, the activator N,N-dimethyl-p-toluidine reacts with dibenzoyl peroxide while forming radicals. The radicals formed initiate radical polymerization of the methyl methacrylate. As the polymerization of the methyl methacrylate proceeds, the viscosity of the bone cement paste increases until it solidifies.

PMMA bone cements may be mixed in suitable mixing bowls using spatulas by mixing the cement powder with the monomer liquid. This may result in air bubbles being entrapped in the bone cement paste, which may negatively affect the mechanical properties of the cured bone cement.

To prevent air entrapment in the bone cement paste, a plurality of vacuum cementing systems have been described, of which the following are mentioned by way of example: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, U.S. Pat. No. 5,344,232 A.

A further development in cementing technology is represented by cementing systems in which both the cement powder and the monomer liquid are already packed in separate compartments of the mixing devices and are not mixed with one another in the cementing system until immediately prior to cement application. Such closed fully prepacked mixing systems have been proposed by EP 0 692 229 A1, DE 10 2009 031 178 B3, U.S. Pat. Nos. 5,997,544 A, 6,709,149 B1, DE 698 12 726 T2, EP 0 796 653 A2, U.S. Pat. No. 5,588,745 A, US 2018/333 176 A1, US 2018/310 974 A1, US 2018/289 406 A1, US 2018/132 919 A1, US 2018/132 917 A1 and US 2018/256 233 A1.

Patent DE 10 2009 031 178 B3 discloses a storage and mixing device as a fully prepacked mixing system, in which the parent components required for producing the bone cement paste are already stored in the storage and mixing device and can be combined and mixed in the storage and mixing device. The storage and mixing device has a two-part delivery plunger for closing a cement cartridge. In this case, a combination of a gas-permeable sterilization plunger and a gas-impermeable sealing plunger is used.

Polymethyl methacrylate bone cements are applied in the not yet cured, paste-like state as a bone cement paste once the cement powder has been mixed with the liquid monomer component. When using mixing devices, the bone cement paste in the case of powder/liquid cements is located in a cartridge. During the production of such conventional PMMA bone cements, once the two parent components have been mixed, the bone cement paste formed is expelled with the aid of manually operable expulsion devices. The bone cement paste is pressed out of the cartridge by the movement of a delivery plunger.

These simple mechanical expulsion devices in particular use clamping rods that are driven by a manually operated rocker arm for expulsion. The manually operated expulsion devices have been tried and tested worldwide for decades and constitute the current state of the art.

In simple vacuum mixing systems, the delivery plunger must be locked in the cartridge during the mixing process in order to prevent withdrawal of the delivery plunger during mixing by a mixing member. Furthermore, the delivery plunger should be fixed in place in the cartridge so that an applied vacuum does not suck the delivery plunger into the interior of the cartridge.

Interlocking locking mechanisms have hitherto been proposed for fixing the delivery plunger in place.

WO 90/13264 A1 proposed tongue-and-groove latching of the delivery plunger. The latched delivery plunger is displaced from its position by axial application of force from a delivery device. The delivery plunger is released as a consequence and can expel the mixed cement paste from the cartridge. Further tongue-and-groove connections were disclosed in EP 0 397 589 B1 and DE 29 21 565 A1.

Patent application WO 01/85070 A1 describes a lug for manual removal which engages in webs of the delivery plunger to latch the latter in place.

DE 10 2012 024 710 A1 discloses a mixing system for a bone cement, in which a delivery plunger can be locked in place with a mixing rod in order to prevent movement of the mixing rod relative to the delivery plunger. The delivery plunger cannot be latched relative to the cartridge by locking the mixing rod to the delivery plunger since the mixing rod, like the delivery plunger, is movable relative to the cartridge.

DE 10 2007 026 034 A1 describes a latching ring, the inner side of which has latching elements and the outer side of which has mating latching elements. The outer latching elements engage in a groove of the cartridge and the inner latching elements in a groove of the delivery plunger. On axial application of force onto the delivery plunger, the latched engagement of the outer or inner latching elements is overcome and the delivery plunger can be axially displaced in the cartridge.

WO 2004/100771 A2 describes a delivery plunger which has latching elements which, on exposure of the delivery plunger to pressure by a hollow cone-shaped disk of a delivery device, are drawn inward out of the latched engagement.

The disadvantage of these systems is that latching acts over a very tightly defined range. The systems therefore have no tolerance with regard to displacement of the delivery plunger. Once the latching point is exceeded, the delivery plunger is released. Instances of incorrect operation may therefore occur in which, on insertion of the delivery plunger or on latching the delivery plunger in place, the latching point is inadvertently exceeded and as a result the delivery plunger is movable in the unlatched state during mixing of the bone cement.

Furthermore, some of the latching devices are of complex construction. There is still a need for inexpensive yet simultaneously reliable solutions.

SUMMARY

One object of one embodiment is therefore to overcome the disadvantages of the prior art. One object of one embodiment is to develop a bone cement applicator and a method with which the delivery plunger can be releasably locked in place in an inexpensive yet reliable manner. Release of the delivery plunger should in one embodiment occur without additional working steps. The bone cement applicator and the method should be provided and suitable for mixing the bone cement paste from the parent components and for delivering the mixed bone cement paste. Construction should be cost-effective so that the device can be used only once for reasons of hygiene.

One embodiment also develops a bone cement applicator for mixing and delivering polymethyl methacrylate bone cement. The bone cement applicator to be developed should permit mixing of the polymethyl methacrylate bone cement powder with the monomer liquid in the interior of a cartridge.

BRIEF DESCRIPTION OF DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

Further exemplary embodiments of one invention are explained below with reference to thirteen schematic figures but without in any way limiting the invention.

DETAILED DESCRIPTION

Figure 1:
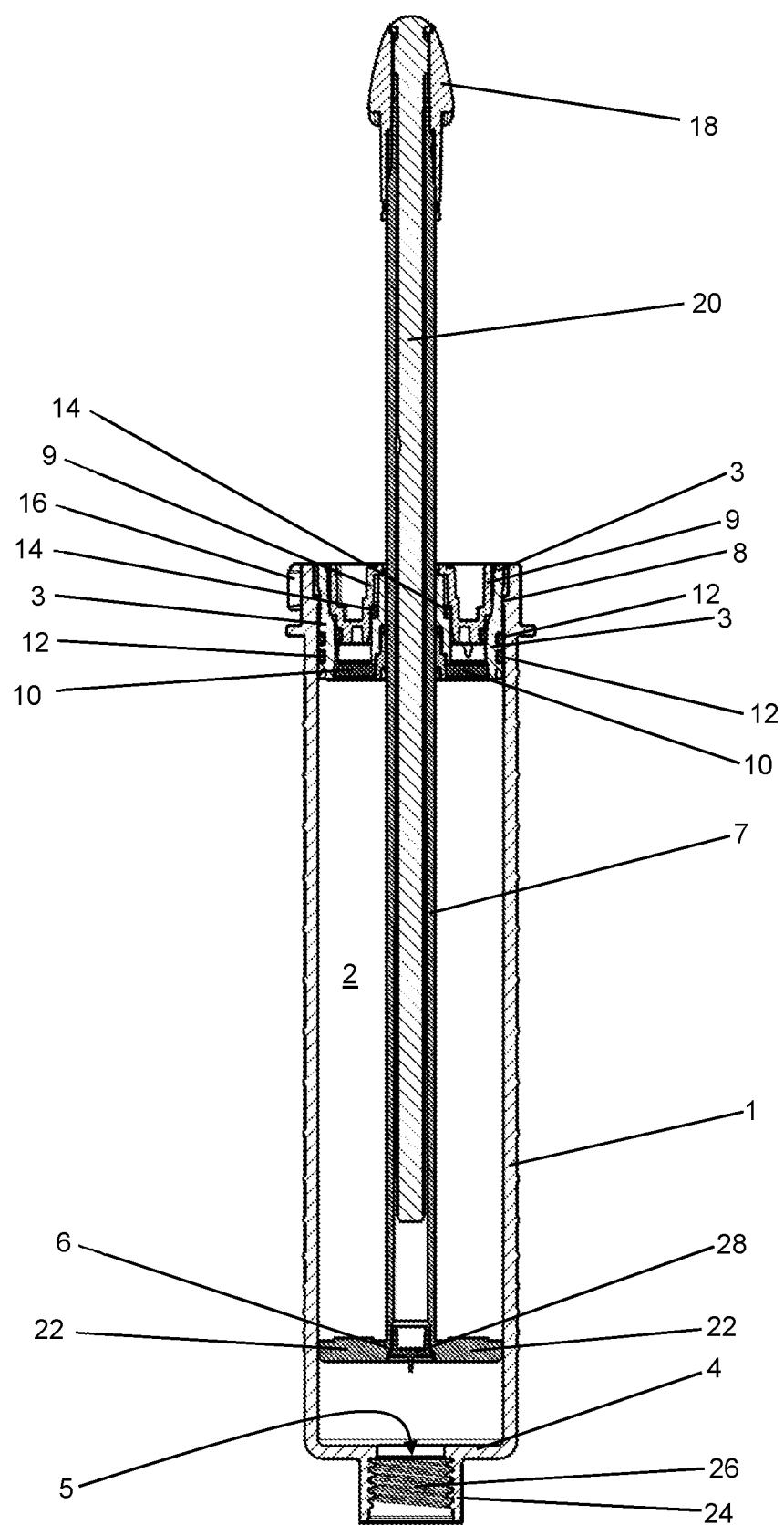
FIG. 1 illustrates a schematic cross-sectional view of a first exemplary bone cement applicator according to one embodiment for mixing and delivering a bone cement with a delivery plunger which is not locked in place.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

Mixing may here be effected by an externally manually actuatable mixing rod with a mixing member mounted thereon. The mixing rod may to this end be guided through the delivery plunger. In one embodiment, it is then necessary to fix the delivery plunger mechanically in place in the cartridge in such a way that the delivery plunger cannot be drawn out of the cartridge during the mixing process. Furthermore, in one embodiment it is important for it not to be possible for the delivery plunger to be drawn into the interior of the cartridge under the effect of the vacuum during mixing of the cement components. After mixing, the delivery plunger should in one embodiment be released by the action of an expulsion device. The cartridge with the delivery plunger should to this end be configured such that the delivery plunger is force-interlockingly fixed in place without an interlocking latched connection. In one embodiment, this force-interlocking fixing must then be configured such that, once the delivery plunger has been pressed out from the fixing region by the action of the expulsion device, the delivery plunger can slide along the inner side of the cartridge without any braking effect by fixing parts.

In one embodiment, the delivery plunger should furthermore be fixable in place in such a way that it cannot be manually pressed out from the fixing region without auxiliary means. Pressing out should only be possible with a mechanical expulsion device which is conventionally used for expelling bone cement.

In one embodiment, the bone cement applicator should here be configured such that it is suitable both as a prepacked cartridge system and as a mixing system to be filled by a medical operator. In the case of the bone cement applicator to be developed being used as a prepacked mixing system, in one embodiment, it should be possible to make use of a two-part delivery plunger according to the teaching of DE 10 2009 031 178 B3.

The objects of one embodiment are achieved by a bone cement applicator for providing a bone cement, in particular a polymethyl methacrylate bone cement, the bone cement applicator having A) a cartridge with a cylindrical interior,
B) a cartridge head with a delivery opening for discharging the bone cement, wherein the cartridge head closes the cylindrical interior of the cartridge at a front side of the cartridge except for the delivery opening,
C) a mixing member which is movably arranged in the cylindrical interior of the cartridge and is movable in the interior with a mixing rod guided into the interior,
D) a delivery plunger which is arranged in the cartridge and is mounted pressably in the direction of the delivery opening in the cylindrical interior of the cartridge, wherein the delivery plunger has an outer cylindrical circumferential surface and wherein the delivery plunger rests at least in places with its outer cylindrical circumferential surface against an inner wall of the cartridge, said inner wall defining the cylindrical interior, and
E) at least one clamping element which is arranged in the region of a back side, opposite the front side of the cartridge, of the cylindrical interior on the inner wall of the cartridge, said inner wall defining the cylindrical interior, wherein the at least one clamping element projects out from the inner wall of the cartridge in the direction of the cylindrical interior, wherein the cylindrical circumferential surface of the delivery plunger is at least in places resiliently deformable by the at least one clamping element in the direction of a central cylinder axis of the cylindrical interior, such that the delivery plunger is clampable in place with the at least one clamping element on the back side of the cartridge.

The delivery plunger is in one embodiment releasably clampable in place with the at least one clamping element on the back side of the cartridge. Releasable means here that, by an axial pressure on the delivery plunger, the delivery plunger is able to be pressed out of the clamping effect produced by the at least one clamping element. Axial pressure means that the piston is pressed or pressable in the direction of the front side of the cartridge along or parallel to the cylinder axis of the cylindrical interior.

Apart from the asymmetry caused by the at least one clamping body, the cylindrical interior of the cartridge has a cylindrical geometry. The cylindrical shape is the simplest shape with which the interior of the cartridge may be made. A cylindrical shape is to be understood geometrically to mean the shape of a general cylinder with any desired base area, meaning not only a cylinder with a circular base area. The inner wall of the interior of the cartridge may thus be formed by the cylinder envelope of a cylinder with any desired base area, in particular with different base areas, meaning also with base areas which are not circular or round. According to one embodiment, however, a cylindrical geometry with a rotationally symmetrical and in particular circular base area is preferred for the interior, since this is the easiest to manufacture.

It may in one embodiment be provided that the mixing rod is guided through the delivery plunger and is mounted axially movably relative to the delivery plunger and is in one embodiment also rotationally movably mounted.

A cement powder for producing the bone cement may in one embodiment be arranged in the cylindrical interior of the cartridge.

The cylindrical circumferential surface of the delivery plunger is at least in places resiliently deformable by the at least one clamping element in the direction of a cylinder axis of the cylindrical interior when the delivery plunger is arranged in the interior of the cartridge with its cylindrical circumferential surface adjacent to the at least one clamping element.

According to a further development of one embodiment, a cement powder may be arranged in the cylindrical interior of the cartridge. The bone cement applicator is in this case a prepacked system, in which only the monomer liquid remains to be added to the cylindrical interior of the cartridge in order to mix the bone cement in the cylindrical interior with the assistance of the mixing member.

It may be provided that the at least one clamping element is formed as one part with the cartridge.

In this manner, a structure which is particularly simple and cost-effective to construct is achieved. In addition, it is possible in this manner to prevent the at least one clamping element from being able to move relative to the inner wall of the cartridge and thereby have its function impaired or modified.

The at least one clamping element is in one embodiment formed as one piece or one part with the cartridge. The position of the at least one clamping element is consequently unambiguously defined. The at least one clamping element may consequently be manufactured straightforwardly together with the cartridge in a plastics injection molding process.

It may further be provided that the delivery opening is closed or closable in the cartridge head with a releasable closure, wherein a thread is in one embodiment arranged on the cartridge head, into or onto which the closure is screwed or screwable with a mating thread which fits the thread, in order to close the delivery opening.

In this manner, the bone cement can be mixed in the cylindrical interior of the cartridge without any of the parent components or the bone cement being able to come out.

The closure is in one embodiment permeable to gases and impermeable to liquids and powders. The interior of the cartridge may accordingly be gas-sterilized through the closure.

It may moreover be provided that the external diameter of the delivery plunger is the same size as or smaller than the internal diameter of the cylindrical interior of the cartridge, wherein in one embodiment at least one circumferential seal and/or a circumferential wiper lip is in one embodiment arranged on the outer circumference of the delivery plunger.

This ensures that the delivery plunger can run in the interior of the cartridge. Due to the circumferential seal and the wiper lip, it can be ensured that no bone cement escapes past the delivery plunger at the back side of the cartridge and that the greatest possible proportion of the bone cement can be discharged from the cartridge and used.

It may in one embodiment also be provided that the internal diameter of the cylindrical interior of the cartridge is reduced in the region of the at least one clamping element by the at least one clamping element, wherein the internal diameter is in one embodiment reduced to such an extent that the delivery plunger has an external diameter larger than the internal diameter reduced by the at least one clamping element.

This ensures that the delivery plunger is clampable in place in the interior of the cartridge while simultaneously also still being able to slide in the interior of the cartridge on application of appropriate force.

In a further development of one embodiment, it may be provided that the at least one clamping element is a circumferential, closed bead or portions of a circumferential bead or at least two circumferential, closed beads spaced apart in an axial direction or at least two portions of a circumferential bead spaced apart in an axial direction.

The bead or the portion may here be formed continuously or also with interruptions. Such clamping elements are simple to manufacture and result in a uniform clamping effect of the delivery plunger. In addition, a clamping effect acting from any radial direction may occur which counteracts possible tilting of the delivery plunger in the interior of the cartridge.

It may further be provided that the at least one clamping element has a chamfer on a front side of the at least one clamping element, said front side facing towards the front side of the cartridge, and a chamfer on a back side of the at least one clamping element, said back side facing towards the back side of the cartridge, wherein the chamfers are arranged perpendicular to the cylinder axis of the cartridge.

This prevents unduly sudden release of the delivery plunger. In addition, the delivery plunger may in this way more readily be brought into the clamped position and the delivery plunger centers itself automatically.

It may also be provided that two or more clamping elements are arranged, axially spaced apart with regard to the cylinder axis of the interior, on the inner wall of the cylindrical interior.

This provides a more stable clamping effect of the delivery plunger and the delivery plunger releases itself in succession from the at least two axially spaced apart clamping elements, such that a jerky release of the clamping effect is reduced. The clamping action is moreover distinctly increased.

According to a further development of one embodiment, it may be provided that an outer wall of the delivery plunger, said outer wall facing towards the inner wall of the cylindrical interior, has an axial extent which is at least the same size as the axial extent of the at least one clamping element, wherein the axial extent of the outer wall of the delivery plunger is in one embodiment at least twice the size of the axial extent of the at least one clamping element.

This ensures that the at least one clamping element can exert the full clamping action on the delivery plunger.

It may moreover be provided that an outer wall of the delivery plunger, said outer wall facing towards the inner wall of the cylindrical interior, is formed as a closed hollow cylinder.

The hollow cylinder may be radially resiliently compressed as a whole and so improve the clamping action.

It may further be provided that the delivery plunger clamped in place by the at least one clamping element is releasable by the action of a force directed along the cylinder axis of the cartridge and is pressable in the direction of the front side of the cartridge.

This ensures that the bone cement applicator may be used with a unidirectional drive without any further and other application of force being necessary.

It may be provided that the outer cylindrical circumferential surface of the delivery plunger consists of a thermoplastic, wherein the thermoplastic is in one embodiment selected from at least one of the plastics materials polyethylene, polypropylene, polyamide, polyethylene terephthalate and polybutylene terephthalate.

Thermoplastics are simple to manufacture and offer the resilience required for the clamping effect.

According to one embodiment, the other parts of the bone cement applicator may also consist of one of the stated plastics materials or of a plurality of these plastics materials polyethylene, polypropylene, polyamide, polyethylene terephthalate and polybutylene terephthalate.

It may also be provided that the bone cement applicator has a sealing plunger which is connectable to the delivery plunger, wherein the delivery plunger includes the outer cylindrical circumferential surface and a passage which is permeable to gases but impermeable to the cement powder and wherein the passage in the delivery plunger is impermeably closable by the sealing plunger, in particular by inserting the sealing plunger into an opening of the delivery plunger, said opening being open in the direction of the back side of the cartridge, wherein the passage is arranged within the opening of the delivery plunger.

This means that the interior of the cartridge, in one embodiment with the cement powder therein, can be sterilized with a sterilizing gas such as ethylene oxide.

The objects of embodiments are also achieved by a method for producing a bone cement, in particular a paste-like polymethyl methacrylate bone cement, wherein the bone cement paste is produced from a cement powder and a monomer liquid using a bone cement applicator according to one embodiment, characterized by the following succession of steps:

A) introducing the cement powder and the monomer liquid into the cylindrical interior of the cartridge or the monomer liquid to the cement powder in the cylindrical interior of the cartridge, B) closing the cartridge by pressing the delivery plunger into the cylindrical interior of the cartridge, C) clamping the delivery plunger in place on the back side of the cartridge with the at least one clamping element, D) mixing the bone cement in the cylindrical interior of the cartridge by moving the mixing member in the cylindrical interior of the cartridge, E) pressing in the delivery plunger in the direction of the front side of the cartridge, wherein the clamping effect of the at least one clamping element is released, and F) expelling the bone cement from the cartridge through the delivery opening by advancing the delivery plunger in the interior of the cartridge in the direction of the cartridge head.

The method is in one embodiment not a medical method. The method particularly in one embodiment has no interaction with a human or animal body. After flowing out of the delivery opening, the bone cement can be pressed through a delivery pipe fastened to the delivery opening or introduced into a container before it is used for cementing.

It may be provided in the method according to one embodiment that the cement powder is introduced into the interior of the cartridge before the monomer liquid or is already present in the cylindrical interior of the cartridge.

This means that the interior of the cartridge can be better utilized and its volume made smaller and more efficient mixing of the bone cement is ensured.

It may further be provided that, on clamping the delivery plunger in place in step C), the delivery plunger is resiliently deformed in the direction of the cylinder axis of the cylindrical interior of the cartridge, wherein a tubular extension on the back side of the delivery plunger, the outer side of which is defined at least in places by the outer cylindrical circumferential surface of the delivery plunger, is in one embodiment pressed by the at least one clamping element in the direction of the cylinder axis of the cylindrical interior of the cartridge.

This means that a particularly effective and simultaneously readily releasable clamping effect is achieved.

It may moreover be provided that, in step D), the mixing member is moved with the mixing rod and then drawn with the mixing rod against a front side of the delivery plunger, said front side facing towards the front side of the cartridge, and then the mixing rod is broken off.

This means that the mixing member and the mixing rod do not interfere during expulsion of the bone cement.

It may also be provided that, before step E), the bone cement applicator is inserted into an expulsion device with an axially movable and drivable ram, wherein in step E) and in step F) the delivery plunger is advanced with the ram.

This means that a powerful movement of the delivery plunger can be used for releasing the clamping effect and for expelling the bone cement.

It may moreover be provided that the delivery opening is closed and is opened before step E) or F).

This means it is possible to prevent any of the bone cement from getting out during mixing thereof.

Underlying one embodiment is the surprising recognition that it is possible by using simple clamping elements to fix the delivery plunger reliably but releasably in place relative to the cartridge with a certain degree of latitude prevailing regarding the fixing position, the delivery plunger thus being fixed in place over a certain path in the interior of the cartridge. As a result, the bone cement can be mixed in the interior of the cartridge without the delivery plunger being released. The delivery plunger can be released by simply pressing it into the interior of the cartridge beyond the clamping position. Due to the resilient deformation which the at least one clamping element exerts on the delivery plunger, once the clamping effect has been released the shape of the delivery plunger can return to its relaxed original state and so be moved in a tight and flush manner in the interior of the cartridge in order to expel the bone cement. The bone cement applicator may accordingly be of inexpensive construction.

On axial application of force by a mechanical expulsion device onto the delivery plunger in the direction of the cartridge head, the delivery plunger is pressed out of its clamped seat and displaced in the direction of the cartridge head. Because the at least one clamping element is attached only to the inner side of the cartridge and the delivery plunger has no projections which have a diameter larger than the internal diameter of the cartridge, the delivery plunger can, once released from the at least one clamping element of the cartridge, be displaced in the direction of the cartridge head without the clamping components having any braking effect.

The advantages of the bone cement applicators and method according to one embodiment are in principle also based on per se known linear movements being used in such a way as to release the delivery plunger and discharge the contents. The bone cement applicator can be used as a hygienic single-use product since it can be manufactured to a very large extent from plastics material and because all parts including the interiors and the cement powder are sterilizable with the aid of ethylene oxide.

A preferred exemplary bone cement applicator according to one embodiment for mixing and delivering polymethyl methacrylate bone cement may be composed of a hollow cylindrical cartridge, a releasable closure in a cartridge head, a mixing rod with a mixing member fastened thereto and a delivery plunger. It may be provided that at least one clamping element is attached to the inner side of the cartridge, wherein the internal diameter of the clamping element is smaller than the internal diameter of the cartridge, the delivery plunger is defined by a cylindrical outer wall, wherein the external diameter of the delivery plunger is the same size as or smaller than the internal diameter of the cartridge, the outer wall of the delivery plunger is resiliently deformable in the direction of the longitudinal axis of the delivery plunger, and the delivery plunger is arranged in the cartridge in such a way that the at least one clamping element resiliently deforms the outer wall of the delivery plunger in the direction of the longitudinal axis of the delivery plunger, wherein the delivery plunger wedges together with the cartridge.

The delivery plunger may be of one-part or also two-part construction according to the teaching of patent DE 10 2009 031 178 B3, to the full teaching and content of which reference is hereby made. It is furthermore or alternatively also possible to guide the mixing rod through the cartridge head and to use as the delivery plunger a simple plunger with a resiliently deformable outer wall, which plunger can be wedged together with the at least one clamping element of the cartridge.

Mixing may here be effected by an externally manually actuatable mixing rod with a mixing member mounted thereon. The mixing rod may to this end be guided through the delivery plunger. In one embodiment, it is then necessary to fix the delivery plunger mechanically in place in the cartridge in such a way that the delivery plunger cannot be drawn out of the cartridge during the mixing process. Furthermore, in one embodiment it is important for it not to be possible for the delivery plunger to be drawn into the interior of the cartridge under the effect of the vacuum during mixing of the cement components. After mixing, the delivery plunger should in one embodiment be released by the action of an expulsion device. The cartridge with the delivery plunger should to this end be configured such that the delivery plunger is force-interlockingly fixed in place without an interlocking latched connection. This force-interlocking fixing in one embodiment must then be configured such that, once the delivery plunger has been pressed out from the fixing region by the action of the expulsion device, the delivery plunger can slide along the inner side of the cartridge without any braking effect by fixing parts.

The delivery plunger should furthermore be fixable in place in such a way that it cannot be manually pressed out from the fixing region without auxiliary means. Pressing out should only be possible with a mechanical expulsion device which is conventionally used for expelling bone cement.

The bone cement applicator should here be configured such that it is suitable both as a prepacked cartridge system and as a mixing system to be filled by a medical operator. In the case of the bone cement applicator to be developed being used as a prepacked mixing system, it should be possible to make use of a two-part delivery plunger according to the teaching of DE 10 2009 031 178 B3.

Objects of one embodiment are achieved by a bone cement applicator for providing a bone cement, in particular a polymethyl methacrylate bone cement, the bone cement applicator having
A) a cartridge with a cylindrical interior,
B) a cartridge head with a delivery opening for discharging the bone cement, wherein the cartridge head closes the cylindrical interior of the cartridge at a front side of the cartridge except for the delivery opening,
C) a mixing member which is movably arranged in the cylindrical interior of the cartridge and is movable in the interior with a mixing rod guided into the interior,
D) a delivery plunger which is arranged in the cartridge and is mounted pressably in the direction of the delivery opening in the cylindrical interior of the cartridge, wherein the delivery plunger has an outer cylindrical circumferential surface and wherein the delivery plunger rests at least in places with its outer cylindrical circumferential surface against an inner wall of the cartridge, said inner wall defining the cylindrical interior, and
E) at least one clamping element which is arranged in the region of a back side, opposite the front side of the cartridge, of the cylindrical interior on the inner wall of the cartridge, said inner wall defining the cylindrical interior, wherein the at least one clamping element projects out from the inner wall of the cartridge in the direction of the cylindrical interior, wherein the cylindrical circumferential surface of the delivery plunger is at least in places resiliently deformable by the at least one clamping element in the direction of a central cylinder axis of the cylindrical interior, such that the delivery plunger is clampable in place with the at least one clamping element on the back side of the cartridge.

The delivery plunger is in one embodiment releasably clampable in place with the at least one clamping element on the back side of the cartridge. Releasable means here that, by an axial pressure on the delivery plunger, the delivery plunger is able to be pressed out of the clamping effect produced by the at least one clamping element. Axial pressure means that the piston is pressed or pressable in the direction of the front side of the cartridge along or parallel to the cylinder axis of the cylindrical interior.

Apart from the asymmetry caused by the at least one clamping body, the cylindrical interior of the cartridge has a cylindrical geometry. The cylindrical shape is the simplest shape with which the interior of the cartridge may be made. A cylindrical shape is to be understood geometrically to mean the shape of a general cylinder with any desired base area, meaning not only a cylinder with a circular base area. The inner wall of the interior of the cartridge may thus be formed by the cylinder envelope of a cylinder with any desired base area, in particular with different base areas, meaning also with base areas which are not circular or round. According to one embodiment, however, a cylindrical geometry with a rotationally symmetrical and in particular circular base area is preferred for the interior, since this is the easiest to manufacture.

It may in one embodiment be provided that the mixing rod is guided through the delivery plunger and is mounted axially movably relative to the delivery plunger and is in one embodiment also rotationally movably mounted.

A cement powder for producing the bone cement may in one embodiment be arranged in the cylindrical interior of the cartridge.

The cylindrical circumferential surface of the delivery plunger is at least in places resiliently deformable by the at least one clamping element in the direction of a cylinder axis of the cylindrical interior when the delivery plunger is arranged in the interior of the cartridge with its cylindrical circumferential surface adjacent to the at least one clamping element.

According to a further development of one embodiment, a cement powder may be arranged in the cylindrical interior of the cartridge. The bone cement applicator is in this case a prepacked system, in which only the monomer liquid remains to be added to the cylindrical interior of the cartridge in order to mix the bone cement in the cylindrical interior with the assistance of the mixing member.

It may be provided that the at least one clamping element is formed as one part with the cartridge.

In this manner, a structure which is particularly simple and cost-effective to construct is achieved. In addition, it is possible in this manner to prevent the at least one clamping element from being able to move relative to the inner wall of the cartridge and thereby have its function impaired or modified.

The at least one clamping element is in one embodiment formed as one piece or one part with the cartridge. The position of the at least one clamping element is consequently unambiguously defined. The at least one clamping element may consequently be manufactured straightforwardly together with the cartridge in a plastics injection molding process.

It may further be provided that the delivery opening is closed or closable in the cartridge head with a releasable closure, wherein a thread is in one embodiment arranged on the cartridge head, into or onto which the closure is screwed or screwable with a mating thread which fits the thread, in order to close the delivery opening.

In this manner, the bone cement can be mixed in the cylindrical interior of the cartridge without any of the parent components or the bone cement being able to come out.

The closure is in one embodiment permeable to gases and impermeable to liquids and powders. The interior of the cartridge may accordingly be gas-sterilized through the closure.

It may moreover be provided that the external diameter of the delivery plunger is the same size as or smaller than the internal diameter of the cylindrical interior of the cartridge, wherein in one embodiment at least one circumferential seal and/or a circumferential wiper lip is in one embodiment arranged on the outer circumference of the delivery plunger.

This ensures that the delivery plunger can run in the interior of the cartridge. Due to the circumferential seal and the wiper lip, it can be ensured that no bone cement escapes past the delivery plunger at the back side of the cartridge and that the greatest possible proportion of the bone cement can be discharged from the cartridge and used.

It may in one embodiment also be provided that the internal diameter of the cylindrical interior of the cartridge is reduced in the region of the at least one clamping element by the at least one clamping element, wherein the internal diameter is in one embodiment reduced to such an extent that the delivery plunger has an external diameter larger than the internal diameter reduced by the at least one clamping element.

This ensures that the delivery plunger is clampable in place in the interior of the cartridge while simultaneously also still being able to slide in the interior of the cartridge on application of appropriate force.

In a further development of one embodiment, it may be provided that the at least one clamping element is a circumferential, closed bead or portions of a circumferential bead or at least two circumferential, closed beads spaced apart in an axial direction or at least two portions of a circumferential bead spaced apart in an axial direction.

The bead or the portion may here be formed continuously or also with interruptions. Such clamping elements are simple to manufacture and result in a uniform clamping effect of the delivery plunger. In addition, a clamping effect acting from any radial direction may occur which counteracts possible tilting of the delivery plunger in the interior of the cartridge.

It may further be provided that the at least one clamping element has a chamfer on a front side of the at least one clamping element, said front side facing towards the front side of the cartridge, and a chamfer on a back side of the at least one clamping element, said back side facing towards the back side of the cartridge, wherein the chamfers are arranged perpendicular to the cylinder axis of the cartridge.

This prevents unduly sudden release of the delivery plunger. In addition, the delivery plunger may in this way more readily be brought into the clamped position and the delivery plunger centers itself automatically.

It may also be provided that two or more clamping elements are arranged, axially spaced apart with regard to the cylinder axis of the interior, on the inner wall of the cylindrical interior.

This provides a more stable clamping effect of the delivery plunger and the delivery plunger releases itself in succession from the at least two axially spaced apart clamping elements, such that a jerky release of the clamping effect is reduced. The clamping action is moreover distinctly increased.

According to a further development of one embodiment, it may be provided that an outer wall of the delivery plunger, said outer wall facing towards the inner wall of the cylindrical interior, has an axial extent which is at least the same size as the axial extent of the at least one clamping element, wherein the axial extent of the outer wall of the delivery plunger is in one embodiment at least twice the size of the axial extent of the at least one clamping element.

This ensures that the at least one clamping element can exert the full clamping action on the delivery plunger.

It may moreover be provided that an outer wall of the delivery plunger, said outer wall facing towards the inner wall of the cylindrical interior, is formed as a closed hollow cylinder.

The hollow cylinder may be radially resiliently compressed as a whole and so improve the clamping action.

It may further be provided that the delivery plunger clamped in place by the at least one clamping element is releasable by the action of a force directed along the cylinder axis of the cartridge and is pressable in the direction of the front side of the cartridge.

This ensures that the bone cement applicator may be used with a unidirectional drive without any further and other application of force being necessary.

It may be provided that the outer cylindrical circumferential surface of the delivery plunger consists of a thermoplastic, wherein the thermoplastic is in one embodiment selected from at least one of the plastics materials polyethylene, polypropylene, polyamide, polyethylene terephthalate and polybutylene terephthalate.

Thermoplastics are simple to manufacture and offer the resilience required for the clamping effect.

According to one embodiment, the other parts of the bone cement applicator may also consist of one of the stated plastics materials or of a plurality of these plastics materials polyethylene, polypropylene, polyamide, polyethylene terephthalate and polybutylene terephthalate.

It may also be provided that the bone cement applicator has a sealing plunger which is connectable to the delivery plunger, wherein the delivery plunger includes the outer cylindrical circumferential surface and a passage which is permeable to gases but impermeable to the cement powder and wherein the passage in the delivery plunger is impermeably closable by the sealing plunger, in particular by inserting the sealing plunger into an opening of the delivery plunger, said opening being open in the direction of the back side of the cartridge, wherein the passage is arranged within the opening of the delivery plunger.

This means that the interior of the cartridge, in one embodiment with the cement powder therein, can be sterilized with a sterilizing gas such as ethylene oxide.

The objects of embodiments are also achieved by a method for producing a bone cement, in particular a paste-like polymethyl methacrylate bone cement, wherein the bone cement paste is produced from a cement powder and a monomer liquid using a bone cement applicator according to one embodiment, characterized by the following succession of steps:

A) introducing the cement powder and the monomer liquid into the cylindrical interior of the cartridge or the monomer liquid to the cement powder in the cylindrical interior of the cartridge, B) closing the cartridge by pressing the delivery plunger into the cylindrical interior of the cartridge, C) clamping the delivery plunger in place on the back side of the cartridge with the at least one clamping element, D) mixing the bone cement in the cylindrical interior of the cartridge by moving the mixing member in the cylindrical interior of the cartridge, E) pressing in the delivery plunger in the direction of the front side of the cartridge, wherein the clamping effect of the at least one clamping element is released, and F) expelling the bone cement from the cartridge through the delivery opening by advancing the delivery plunger in the interior of the cartridge in the direction of the cartridge head.

The method is in one embodiment not a medical method. The method particularly in one embodiment has no interaction with a human or animal body. After flowing out of the delivery opening, the bone cement can be pressed through a delivery pipe fastened to the delivery opening or introduced into a container before it is used for cementing.

It may be provided in the method according to one embodiment that the cement powder is introduced into the interior of the cartridge before the monomer liquid or is already present in the cylindrical interior of the cartridge.

This means that the interior of the cartridge can be better utilized and its volume made smaller and more efficient mixing of the bone cement is ensured.

It may further be provided that, on clamping the delivery plunger in place in step C), the delivery plunger is resiliently deformed in the direction of the cylinder axis of the cylindrical interior of the cartridge, wherein a tubular extension on the back side of the delivery plunger, the outer side of which is defined at least in places by the outer cylindrical circumferential surface of the delivery plunger, is in one embodiment pressed by the at least one clamping element in the direction of the cylinder axis of the cylindrical interior of the cartridge.

This means that a particularly effective and simultaneously readily releasable clamping effect is achieved.

It may moreover be provided that, in step D), the mixing member is moved with the mixing rod and then drawn with the mixing rod against a front side of the delivery plunger, said front side facing towards the front side of the cartridge, and then the mixing rod is broken off.

This means that the mixing member and the mixing rod do not interfere during expulsion of the bone cement.

It may also be provided that, before step E), the bone cement applicator is inserted into an expulsion device with an axially movable and drivable ram, wherein in step E) and in step F) the delivery plunger is advanced with the ram.

This means that a powerful movement of the delivery plunger can be used for releasing the clamping effect and for expelling the bone cement.

It may moreover be provided that the delivery opening is closed and is opened before step E) or F).

This means it is possible to prevent any of the bone cement from getting out during mixing thereof.

Underlying one embodiment is the surprising recognition that it is possible by using simple clamping elements to fix the delivery plunger reliably but releasably in place relative to the cartridge with a certain degree of latitude prevailing regarding the fixing position, the delivery plunger thus being fixed in place over a certain path in the interior of the cartridge. As a result, the bone cement can be mixed in the interior of the cartridge without the delivery plunger being released. The delivery plunger can be released by simply pressing it into the interior of the cartridge beyond the clamping position. Due to the resilient deformation which the at least one clamping element exerts on the delivery plunger, once the clamping effect has been released the shape of the delivery plunger can return to its relaxed original state and so be moved in a tight and flush manner in the interior of the cartridge in order to expel the bone cement. The bone cement applicator may accordingly be of inexpensive construction.

On axial application of force by a mechanical expulsion device onto the delivery plunger in the direction of the cartridge head, the delivery plunger is pressed out of its clamped seat and displaced in the direction of the cartridge head. Because the at least one clamping element is attached only to the inner side of the cartridge and the delivery plunger has no projections which have a diameter larger than the internal diameter of the cartridge, the delivery plunger can, once released from the at least one clamping element of the cartridge, be displaced in the direction of the cartridge head without the clamping components having any braking effect.

The advantages of the bone cement applicators and method according to one embodiment are in principle also based on per se known linear movements being used in such a way as to release the delivery plunger and discharge the contents. The bone cement applicator can be used as a hygienic single-use product since it can be manufactured to a very large extent from plastics material and because all parts including the interiors and the cement powder are sterilizable with the aid of ethylene oxide.

A preferred exemplary bone cement applicator according to one embodiment for mixing and delivering polymethyl methacrylate bone cement may be composed of a hollow cylindrical cartridge, a releasable closure in a cartridge head, a mixing rod with a mixing member fastened thereto and a delivery plunger. It may be provided that at least one clamping element is attached to the inner side of the cartridge, wherein the internal diameter of the clamping element is smaller than the internal diameter of the cartridge, the delivery plunger is defined by a cylindrical outer wall, wherein the external diameter of the delivery plunger is the same size as or smaller than the internal diameter of the cartridge, the outer wall of the delivery plunger is resiliently deformable in the direction of the longitudinal axis of the delivery plunger, and the delivery plunger is arranged in the cartridge in such a way that the at least one clamping element resiliently deforms the outer wall of the delivery plunger in the direction of the longitudinal axis of the delivery plunger, wherein the delivery plunger wedges together with the cartridge.

The delivery plunger may be of one-part or also two-part construction according to the teaching of patent DE 10 2009 031 178 B3, to the full teaching and content of which reference is hereby made. It is furthermore or alternatively also possible to guide the mixing rod through the cartridge head and to use as the delivery plunger a simple plunger with a resiliently deformable outer wall, which plunger can be wedged together with the at least one clamping element of the cartridge.

Mixing may here be effected by an externally manually actuatable mixing rod with a mixing member mounted thereon. The mixing rod may to this end be guided through the delivery plunger. In one embodiment, it is then necessary to fix the delivery plunger mechanically in place in the cartridge in such a way that the delivery plunger cannot be drawn out of the cartridge during the mixing process. Furthermore, in one embodiment it is important for it not to be possible for the delivery plunger to be drawn into the interior of the cartridge under the effect of the vacuum during mixing of the cement components. After mixing, the delivery plunger should in one embodiment be released by the action of an expulsion device. The cartridge with the delivery plunger should to this end be configured such that the delivery plunger is force-interlockingly fixed in place without an interlocking latched connection. This force-interlocking fixing in one embodiment must then be configured such that, once the delivery plunger has been pressed out from the fixing region by the action of the expulsion device, the delivery plunger can slide along the inner side of the cartridge without any braking effect by fixing parts.

The delivery plunger should furthermore be fixable in place in such a way that it cannot be manually pressed out from the fixing region without auxiliary means. Pressing out should only be possible with a mechanical expulsion device which is conventionally used for expelling bone cement.

The bone cement applicator should here be configured such that it is suitable both as a prepacked cartridge system and as a mixing system to be filled by a medical operator. In the case of the bone cement applicator to be developed being used as a prepacked mixing system, it should be possible to make use of a two-part delivery plunger according to the teaching of DE 10 2009 031 178 B3.

Objects of one embodiment are achieved by a bone cement applicator for providing a bone cement, in particular a polymethyl methacrylate bone cement, the bone cement applicator having A) a cartridge with a cylindrical interior, B) a cartridge head with a delivery opening for discharging the bone cement, wherein the cartridge head closes the cylindrical interior of the cartridge at a front side of the cartridge except for the delivery opening, C) a mixing member which is movably arranged in the cylindrical interior of the cartridge and is movable in the interior with a mixing rod guided into the interior, D) a delivery plunger which is arranged in the cartridge and is mounted pressably in the direction of the delivery opening in the cylindrical interior of the cartridge, wherein the delivery plunger has an outer cylindrical circumferential surface and wherein the delivery plunger rests at least in places with its outer cylindrical circumferential surface against an inner wall of the cartridge, said inner wall defining the cylindrical interior, and E) at least one clamping element which is arranged in the region of a back side, opposite the front side of the cartridge, of the cylindrical interior on the inner wall of the cartridge, said inner wall defining the cylindrical interior, wherein the at least one clamping element projects out from the inner wall of the cartridge in the direction of the cylindrical interior, wherein the cylindrical circumferential surface of the delivery plunger is at least in places resiliently deformable by the at least one clamping element in the direction of a central cylinder axis of the cylindrical interior, such that the delivery plunger is clampable in place with the at least one clamping element on the back side of the cartridge.

The delivery plunger is in one embodiment releasably clampable in place with the at least one clamping element on the back side of the cartridge. Releasable means here that, by an axial pressure on the delivery plunger, the delivery plunger is able to be pressed out of the clamping effect produced by the at least one clamping element. Axial pressure means that the piston is pressed or pressable in the direction of the front side of the cartridge along or parallel to the cylinder axis of the cylindrical interior.

Apart from the asymmetry caused by the at least one clamping body, the cylindrical interior of the cartridge has a cylindrical geometry. The cylindrical shape is the simplest shape with which the interior of the cartridge may be made. A cylindrical shape is to be understood geometrically to mean the shape of a general cylinder with any desired base area, meaning not only a cylinder with a circular base area. The inner wall of the interior of the cartridge may thus be formed by the cylinder envelope of a cylinder with any desired base area, in particular with different base areas, meaning also with base areas which are not circular or round. According to one embodiment, however, a cylindrical geometry with a rotationally symmetrical and in particular circular base area is preferred for the interior, since this is the easiest to manufacture.

It may in one embodiment be provided that the mixing rod is guided through the delivery plunger and is mounted axially movably relative to the delivery plunger and is in one embodiment also rotationally movably mounted.

A cement powder for producing the bone cement may in one embodiment be arranged in the cylindrical interior of the cartridge.

The cylindrical circumferential surface of the delivery plunger is at least in places resiliently deformable by the at least one clamping element in the direction of a cylinder axis of the cylindrical interior when the delivery plunger is arranged in the interior of the cartridge with its cylindrical circumferential surface adjacent to the at least one clamping element.

According to a further development of one embodiment, a cement powder may be arranged in the cylindrical interior of the cartridge. The bone cement applicator is in this case a prepacked system, in which only the monomer liquid remains to be added to the cylindrical interior of the cartridge in order to mix the bone cement in the cylindrical interior with the assistance of the mixing member.

It may be provided that the at least one clamping element is formed as one part with the cartridge.

In this manner, a structure which is particularly simple and cost-effective to construct is achieved. In addition, it is possible in this manner to prevent the at least one clamping element from being able to move relative to the inner wall of the cartridge and thereby have its function impaired or modified.

The at least one clamping element is in one embodiment formed as one piece or one part with the cartridge. The position of the at least one clamping element is consequently unambiguously defined. The at least one clamping element may consequently be manufactured straightforwardly together with the cartridge in a plastics injection molding process.

It may further be provided that the delivery opening is closed or closable in the cartridge head with a releasable closure, wherein a thread is in one embodiment arranged on the cartridge head, into or onto which the closure is screwed or screwable with a mating thread which fits the thread, in order to close the delivery opening.

In this manner, the bone cement can be mixed in the cylindrical interior of the cartridge without any of the parent components or the bone cement being able to come out.

The closure is in one embodiment permeable to gases and impermeable to liquids and powders. The interior of the cartridge may accordingly be gas-sterilized through the closure.

It may moreover be provided that the external diameter of the delivery plunger is the same size as or smaller than the internal diameter of the cylindrical interior of the cartridge, wherein in one embodiment at least one circumferential seal and/or a circumferential wiper lip is in one embodiment arranged on the outer circumference of the delivery plunger.

This ensures that the delivery plunger can run in the interior of the cartridge. Due to the circumferential seal and the wiper lip, it can be ensured that no bone cement escapes past the delivery plunger at the back side of the cartridge and that the greatest possible proportion of the bone cement can be discharged from the cartridge and used.

It may in one embodiment also be provided that the internal diameter of the cylindrical interior of the cartridge is reduced in the region of the at least one clamping element by the at least one clamping element, wherein the internal diameter is in one embodiment reduced to such an extent that the delivery plunger has an external diameter larger than the internal diameter reduced by the at least one clamping element.

This ensures that the delivery plunger is clampable in place in the interior of the cartridge while simultaneously also still being able to slide in the interior of the cartridge on application of appropriate force.

In a further development of one embodiment, it may be provided that the at least one clamping element is a circumferential, closed bead or portions of a circumferential bead or at least two circumferential, closed beads spaced apart in an axial direction or at least two portions of a circumferential bead spaced apart in an axial direction.

The bead or the portion may here be formed continuously or also with interruptions. Such clamping elements are simple to manufacture and result in a uniform clamping effect of the delivery plunger. In addition, a clamping effect acting from any radial direction may occur which counteracts possible tilting of the delivery plunger in the interior of the cartridge.

It may further be provided that the at least one clamping element has a chamfer on a front side of the at least one clamping element, said front side facing towards the front side of the cartridge, and a chamfer on a back side of the at least one clamping element, said back side facing towards the back side of the cartridge, wherein the chamfers are arranged perpendicular to the cylinder axis of the cartridge.

This prevents unduly sudden release of the delivery plunger. In addition, the delivery plunger may in this way more readily be brought into the clamped position and the delivery plunger centers itself automatically.

It may also be provided that two or more clamping elements are arranged, axially spaced apart with regard to the cylinder axis of the interior, on the inner wall of the cylindrical interior.

This provides a more stable clamping effect of the delivery plunger and the delivery plunger releases itself in succession from the at least two axially spaced apart clamping elements, such that a jerky release of the clamping effect is reduced. The clamping action is moreover distinctly increased.

According to a further development of one embodiment, it may be provided that an outer wall of the delivery plunger, said outer wall facing towards the inner wall of the cylindrical interior, has an axial extent which is at least the same size as the axial extent of the at least one clamping element, wherein the axial extent of the outer wall of the delivery plunger is in one embodiment at least twice the size of the axial extent of the at least one clamping element.

This ensures that the at least one clamping element can exert the full clamping action on the delivery plunger.

It may moreover be provided that an outer wall of the delivery plunger, said outer wall facing towards the inner wall of the cylindrical interior, is formed as a closed hollow cylinder.

The hollow cylinder may be radially resiliently compressed as a whole and so improve the clamping action.

It may further be provided that the delivery plunger clamped in place by the at least one clamping element is releasable by the action of a force directed along the cylinder axis of the cartridge and is pressable in the direction of the front side of the cartridge.

This ensures that the bone cement applicator may be used with a unidirectional drive without any further and other application of force being necessary.

It may be provided that the outer cylindrical circumferential surface of the delivery plunger consists of a thermoplastic, wherein the thermoplastic is in one embodiment selected from at least one of the plastics materials polyethylene, polypropylene, polyamide, polyethylene terephthalate and polybutylene terephthalate.

Thermoplastics are simple to manufacture and offer the resilience required for the clamping effect.

According to one embodiment, the other parts of the bone cement applicator may also consist of one of the stated plastics materials or of a plurality of these plastics materials polyethylene, polypropylene, polyamide, polyethylene terephthalate and polybutylene terephthalate.

It may also be provided that the bone cement applicator has a sealing plunger which is connectable to the delivery plunger, wherein the delivery plunger includes the outer cylindrical circumferential surface and a passage which is permeable to gases but impermeable to the cement powder and wherein the passage in the delivery plunger is impermeably closable by the sealing plunger, in particular by inserting the sealing plunger into an opening of the delivery plunger, said opening being open in the direction of the back side of the cartridge, wherein the passage is arranged within the opening of the delivery plunger.

This means that the interior of the cartridge, in one embodiment with the cement powder therein, can be sterilized with a sterilizing gas such as ethylene oxide.

Objects of one embodiment are also achieved by a method for producing a bone cement, in particular a paste-like polymethyl methacrylate bone cement, wherein the bone cement paste is produced from a cement powder and a monomer liquid using a bone cement applicator according to one embodiment, characterized by the following succession of steps:

A) introducing the cement powder and the monomer liquid into the cylindrical interior of the cartridge or the monomer liquid to the cement powder in the cylindrical interior of the cartridge, B) closing the cartridge by pressing the delivery plunger into the cylindrical interior of the cartridge, C) clamping the delivery plunger in place on the back side of the cartridge with the at least one clamping element, D) mixing the bone cement in the cylindrical interior of the cartridge by moving the mixing member in the cylindrical interior of the cartridge, E) pressing in the delivery plunger in the direction of the front side of the cartridge, wherein the clamping effect of the at least one clamping element is released, and F) expelling the bone cement from the cartridge through the delivery opening by advancing the delivery plunger in the interior of the cartridge in the direction of the cartridge head.

The method is in one embodiment not a medical method. The method particularly in one embodiment has no interaction with a human or animal body. After flowing out of the delivery opening, the bone cement can be pressed through a delivery pipe fastened to the delivery opening or introduced into a container before it is used for cementing.

It may be provided in the method according to one embodiment that the cement powder is introduced into the interior of the cartridge before the monomer liquid or is already present in the cylindrical interior of the cartridge.

This means that the interior of the cartridge can be better utilized and its volume made smaller and more efficient mixing of the bone cement is ensured.

It may further be provided that, on clamping the delivery plunger in place in step C), the delivery plunger is resiliently deformed in the direction of the cylinder axis of the cylindrical interior of the cartridge, wherein a tubular extension on the back side of the delivery plunger, the outer side of which is defined at least in places by the outer cylindrical circumferential surface of the delivery plunger, is in one embodiment pressed by the at least one clamping element in the direction of the cylinder axis of the cylindrical interior of the cartridge.

This means that a particularly effective and simultaneously readily releasable clamping effect is achieved.

It may moreover be provided that, in step D), the mixing member is moved with the mixing rod and then drawn with the mixing rod against a front side of the delivery plunger, said front side facing towards the front side of the cartridge, and then the mixing rod is broken off.

This means that the mixing member and the mixing rod do not interfere during expulsion of the bone cement.

It may also be provided that, before step E), the bone cement applicator is inserted into an expulsion device with an axially movable and drivable ram, wherein in step E) and in step F) the delivery plunger is advanced with the ram.

This means that a powerful movement of the delivery plunger can be used for releasing the clamping effect and for expelling the bone cement.

It may moreover be provided that the delivery opening is closed and is opened before step E) or F).

This means it is possible to prevent any of the bone cement from getting out during mixing thereof.

Underlying one embodiment is the surprising recognition that it is possible by using simple clamping elements to fix the delivery plunger reliably but releasably in place relative to the cartridge with a certain degree of latitude prevailing regarding the fixing position, the delivery plunger thus being fixed in place over a certain path in the interior of the cartridge. As a result, the bone cement can be mixed in the interior of the cartridge without the delivery plunger being released. The delivery plunger can be released by simply pressing it into the interior of the cartridge beyond the clamping position. Due to the resilient deformation which the at least one clamping element exerts on the delivery plunger, once the clamping effect has been released the shape of the delivery plunger can return to its relaxed original state and so be moved in a tight and flush manner in the interior of the cartridge in order to expel the bone cement. The bone cement applicator may accordingly be of inexpensive construction.

On axial application of force by a mechanical expulsion device onto the delivery plunger in the direction of the cartridge head, the delivery plunger is pressed out of its clamped seat and displaced in the direction of the cartridge head. Because the at least one clamping element is attached only to the inner side of the cartridge and the delivery plunger has no projections which have a diameter larger than the internal diameter of the cartridge, the delivery plunger can, once released from the at least one clamping element of the cartridge, be displaced in the direction of the cartridge head without the clamping components having any braking effect.

The advantages of the bone cement applicators and method according to one embodiment are in principle also based on per se known linear movements being used in such a way as to release the delivery plunger and discharge the contents. The bone cement applicator can be used as a hygienic single-use product since it can be manufactured to a very large extent from plastics material and because all parts including the interiors and the cement powder are sterilizable with the aid of ethylene oxide.

A preferred exemplary bone cement applicator according to one embodiment for mixing and delivering polymethyl methacrylate bone cement may be composed of a hollow cylindrical cartridge, a releasable closure in a cartridge head, a mixing rod with a mixing member fastened thereto and a delivery plunger. It may be provided that at least one clamping element is attached to the inner side of the cartridge, wherein the internal diameter of the clamping element is smaller than the internal diameter of the cartridge, the delivery plunger is defined by a cylindrical outer wall, wherein the external diameter of the delivery plunger is the same size as or smaller than the internal diameter of the cartridge, the outer wall of the delivery plunger is resiliently deformable in the direction of the longitudinal axis of the delivery plunger, and the delivery plunger is arranged in the cartridge in such a way that the at least one clamping element resiliently deforms the outer wall of the delivery plunger in the direction of the longitudinal axis of the delivery plunger, wherein the delivery plunger wedges together with the cartridge.

The delivery plunger may be of one-part or also two-part construction according to the teaching of patent DE 10 2009 031 178 B3, to the full teaching and content of which reference is hereby made. It is furthermore or alternatively also possible to guide the mixing rod through the cartridge head and to use as the delivery plunger a simple plunger with a resiliently deformable outer wall, which plunger can be wedged together with the at least one clamping element of the cartridge.

Figure 5:
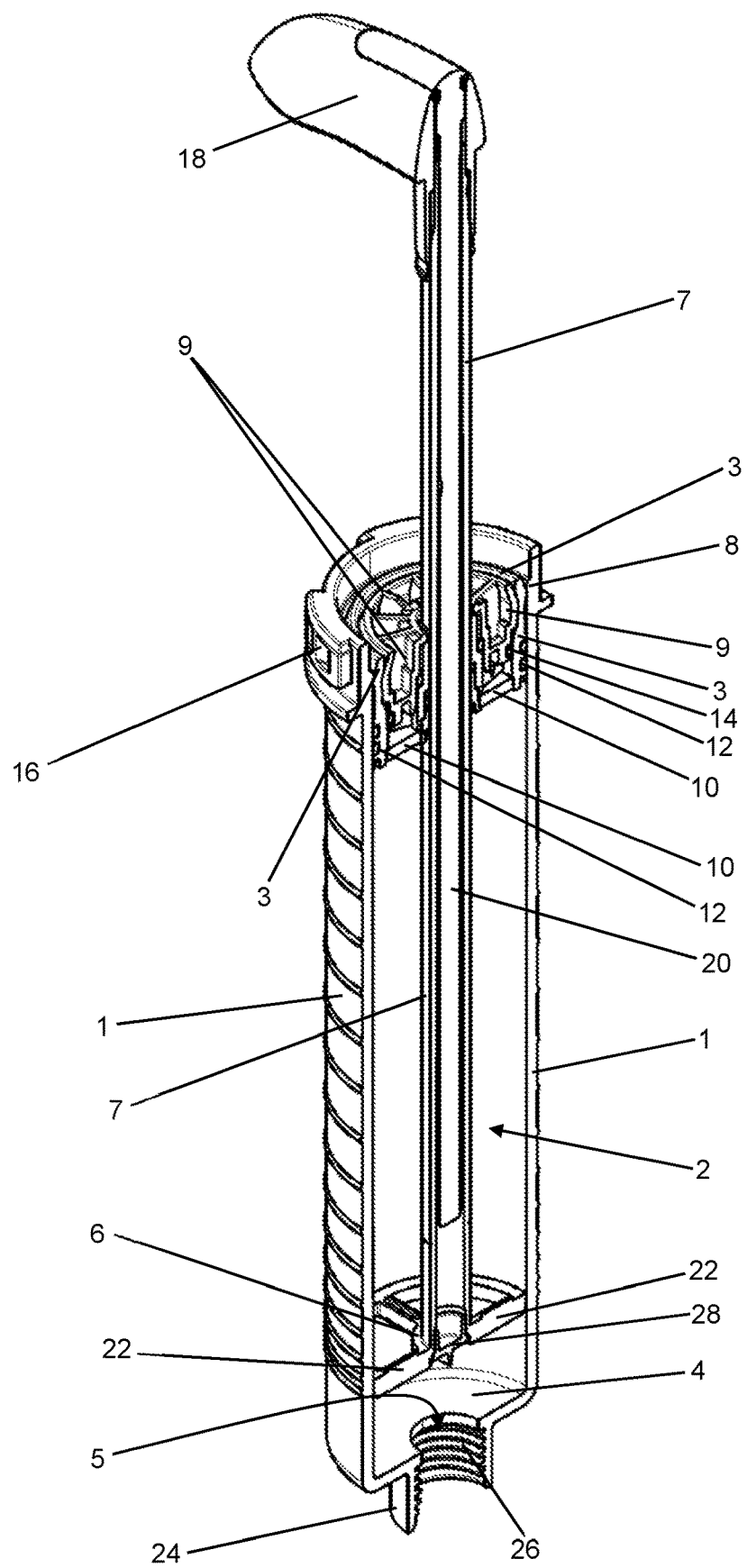
FIG. 5 illustrates a schematic perspective cross-sectional view of the bone cement applicator according to FIG. 4.
Figure 6:
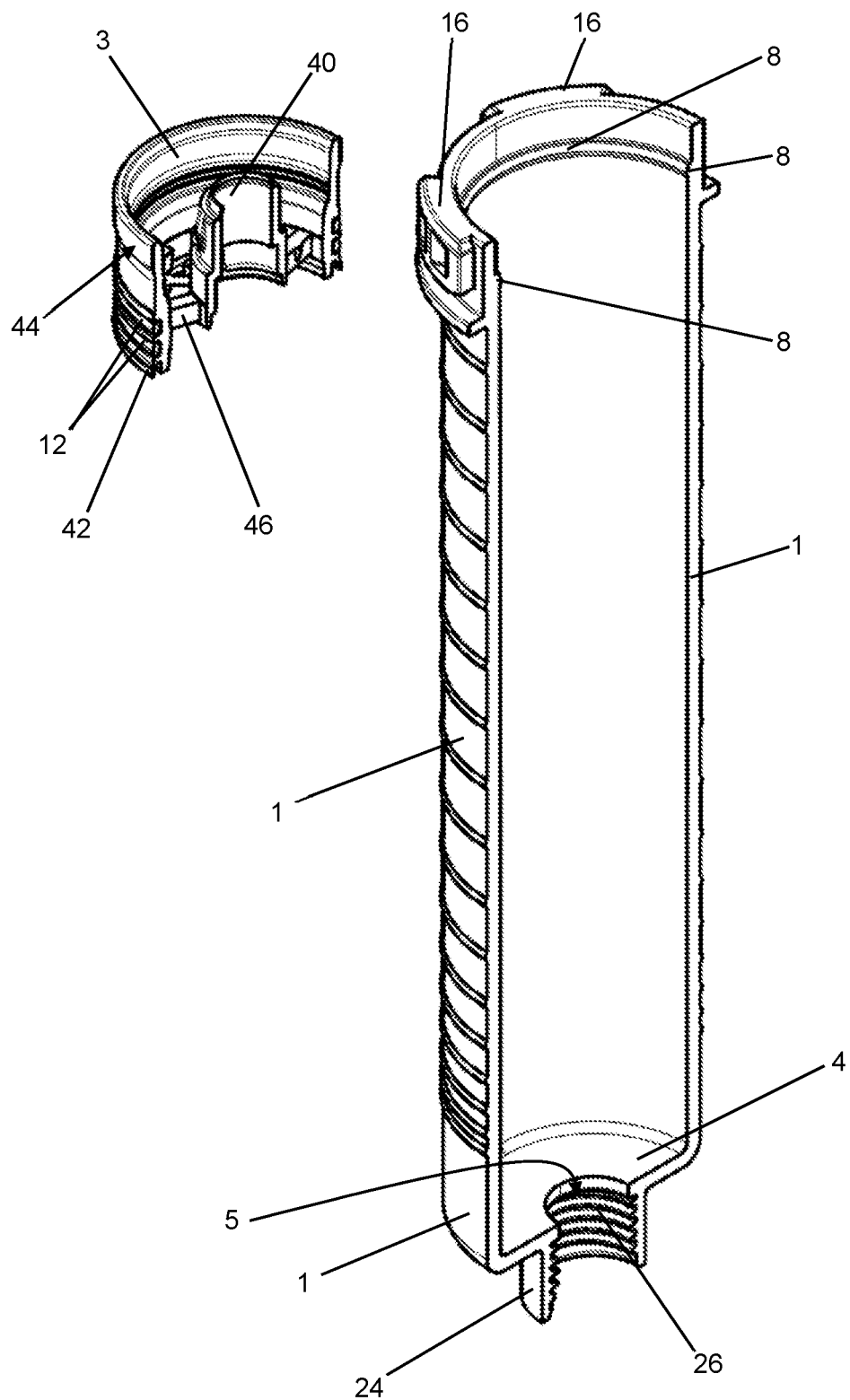
FIG. 6 illustrates the cartridge and the delivery plunger of the bone cement applicator according to FIG. 4 as individual schematic perspective cross-sectional views.
Figure 7:
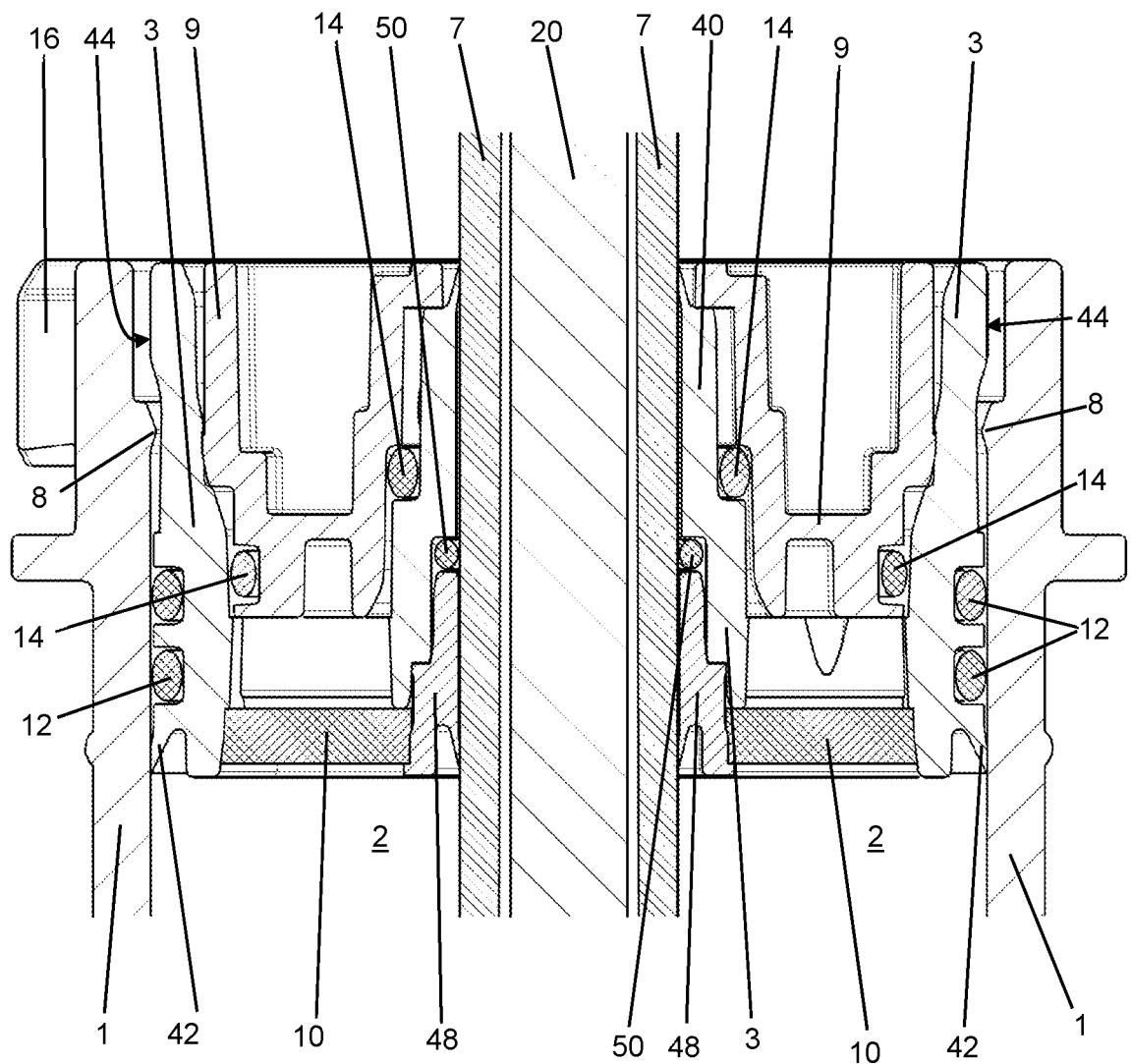
FIG. 7 illustrates an enlarged detail of FIG. 1 in the region of the unlocked delivery plunger.
Figure 8:
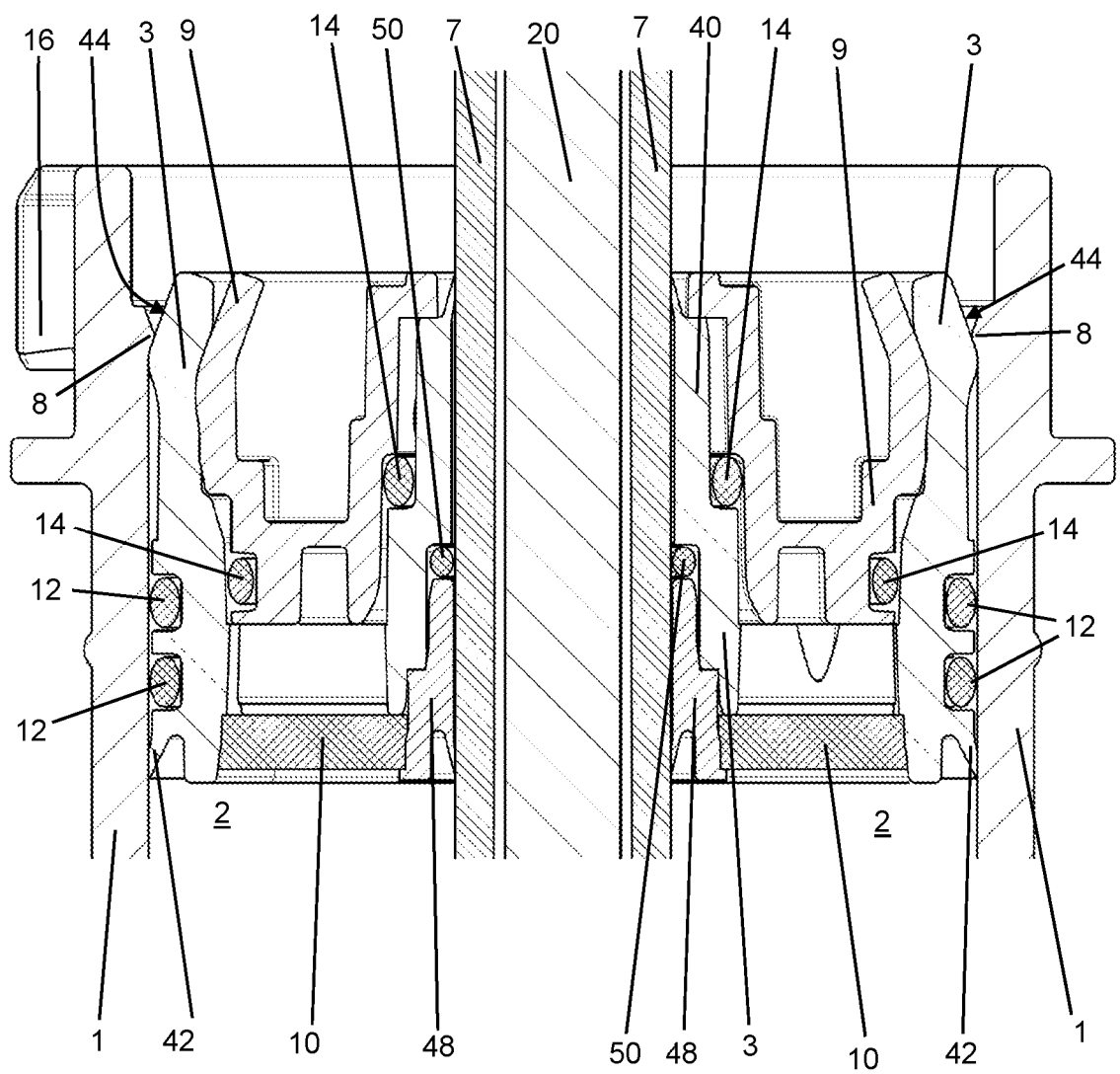
FIG. 8 illustrates an enlarged detail of FIG. 2 in the region of the locked delivery plunger.
Figure 9:
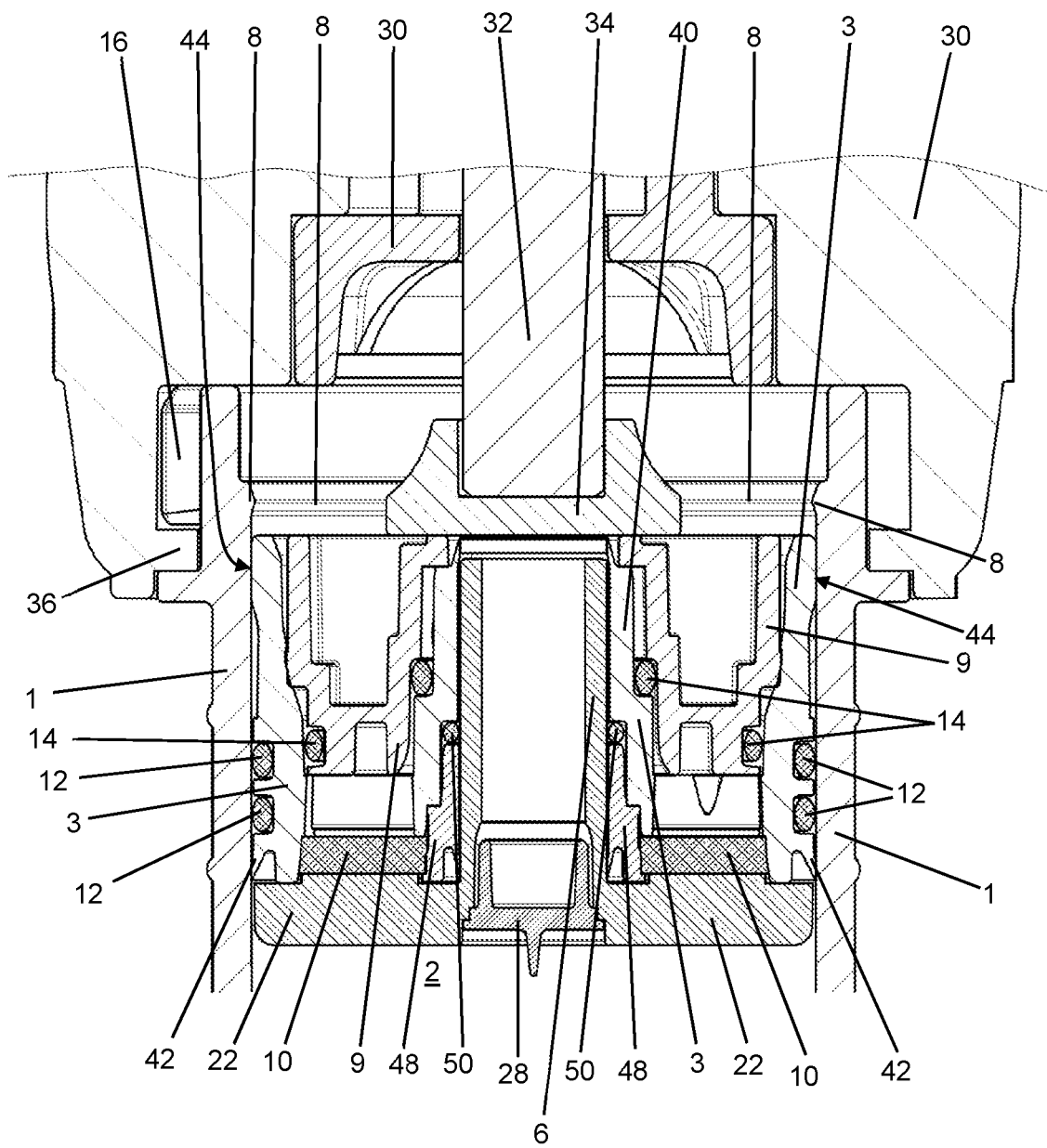
FIG. 9 illustrates an enlarged detail of FIG. 3 in the region of the delivery plunger driven with the expulsion device.

FIGS. 1 to 9 show illustrations of a first bone cement applicator according to one embodiment. FIGS. 1 to 5 show various schematic overall views of the first exemplary bone cement applicator according to one embodiment. FIG. 6 illustrates cross-sectional views of two parts of the bone cement applicator and FIGS. 7 to 9 show enlarged details of FIGS. 1 to 3 in the form of schematic cross-sectional views as detail views through a region of the bone cement applicator according to one embodiment. In all the figures, the front side of the bone cement applicator is arranged at the bottom and the back side of the bone cement applicator at the top.

According to the first exemplary embodiment of the present invention, the bone cement applicator may have a tubular cartridge 1 of a plastics material with a cylindrical interior 2. A delivery plunger 3 mounted so as to be movable in an axial direction may be arranged in the cylindrical interior 2 of the cartridge 1. At a front side of the cartridge (at the bottom in the figures), the cylindrical interior 2 may be closed by a cartridge head 4 which may be of one-part construction with the cartridge. Alternatively, the cartridge head 4 may also be screwed onto the cartridge 1 as a separate part. A delivery opening 5 may be arranged in the cartridge head 4, through which opening a bone cement (not shown in the figures), which may be present or mixed in the cylindrical interior 2 of the cartridge 1, may be discharged from the interior 2 with the delivery plunger 3. The delivery opening 5 may be closable or closed. A cement powder (not shown) as parent component of the bone cement to be produced may be arranged in the cylindrical interior 2 of the cartridge 1. A monomer liquid (not shown) as second parent component can be added to the cement powder in the cylindrical interior 2 in order to mix the bone cement in the interior.

A mixing member 6 may be movably arranged in the cylindrical interior 2 for intermixing the contents of the interior 2. The mixing member 6 may be moved axially with a mixing rod 7 in the cylindrical interior 2 and rotated about the axis of the mixing rod 7. The mixing rod 7 may be guided through a leadthrough in the delivery plunger 3 into the interior 2 of the cartridge 1. Alternatively, the mixing rod 7 could also be guided through the cartridge head (see the third exemplary embodiment according to FIGS. 11 and 12).

A projecting circumferential rail as clamping element 8 for clamping the delivery plunger 3 in place may be arranged on the inner wall of the cartridge 1 in the region of the rear end of the cartridge 1 (at the top in the figures). When the delivery plunger 3 is pressed into the rear end of the cartridge 1, the clamping element 8 may exert radial pressure onto the delivery plunger 3. The delivery plunger 3 can be resiliently deformed by the radial pressure. The resilient deformation of the delivery plunger 3 may clamp the delivery plunger 3 at the level of the clamping element 8.

In the back side of the delivery plunger 3, a sealing plunger 9 may be arranged with which a passage through the delivery plunger 3 may be sealed. A porous filter 10 which is permeable to gases but impermeable to the cement powder may be arranged in the passage through the delivery plunger 3. The interior 2 of the cartridge 1 and the contents thereof may be sterilized with the assistance of a sterilizing gas such as ethylene oxide through the passage in the delivery plunger 3 and optionally through the porous filter 10. The sealing plunger 9 may then be inserted to seal the passage. When the passage is sealed, the interior 2 of the cartridge 1 can be evacuated in order to permit mixing of the bone cement under a vacuum.

In order to enable evacuation of the interior 2, two circumferential seals 12 of rubber may be arranged on the outer wall of the delivery plunger 3, said seals sealing the delivery plunger 3 relative to the inner wall of the cartridge 1 and thus the cylindrical interior 2. The sealing plunger 9 may likewise be sealed relative to the delivery plunger 3 with a circumferential seal 14. The delivery plunger 3 may further be sealed relative to the mixing rod 7 with a circumferential seal 50 (see detail views of FIGS. 7, 8 and 9).

A plurality of fastening means 16 to which an expulsion device 30 may be fastened (see FIG. 9) may be arranged externally on the back side of the cartridge 1.

The mixing rod 7 may terminate in a handle 18 with which the mixing rod 7 and thus the mixing member 6 may be moved in the interior 2 of the cartridge 1. A core 20 which mechanically stabilizes the mixing rod 7 may be arranged in the interior of the mixing rod 7. The mixing rod 7 may be movably mounted in a leadthrough through the delivery plunger 3. The mixing rod 7 may be moved axially through the leadthrough through the delivery plunger 3 and in one embodiment also be rotated in the leadthrough. If the mixing member 6 is rigidly connected to the mixing rod 7, the mixing member 6 may accordingly be moved axially and in one embodiment also rotated in the interior 2 of the cartridge 1. This way, the contents of the cartridge 1 are manually mixable with the mixing member 6. The mixing member 6 may have a plurality of mixing blades 22 which serve to intermix the interior 2. The mixing member 6 may have a circumferential ring which rests against the wall of the cylindrical interior 2. As a consequence, all regions of the interior 2 can be reached with the mixing member 6 and thus complete intermixing of the bone cement in the interior 2 can be ensured.

A fitting 24 may be arranged on the cartridge head 4. The delivery opening 5 may be arranged in the interior of the fitting 24. An internal thread 26 for fastening a delivery pipe (not shown) may be arranged in the fitting 24. The bone cement may be applied via the delivery pipe or guided into a tray for subsequent use. The delivery opening 5 may be closed with a closure (not shown). For example, a screwable closure with an external thread can be screwed into the internal thread 26 of the fitting 24. The closure can be removed once the bone cement has been completely mixed.

The mixing rod 7 may be closed on the front side thereof with a plug 28 so that the bone cement does not get into the mixing rod 7.

Figure 2:
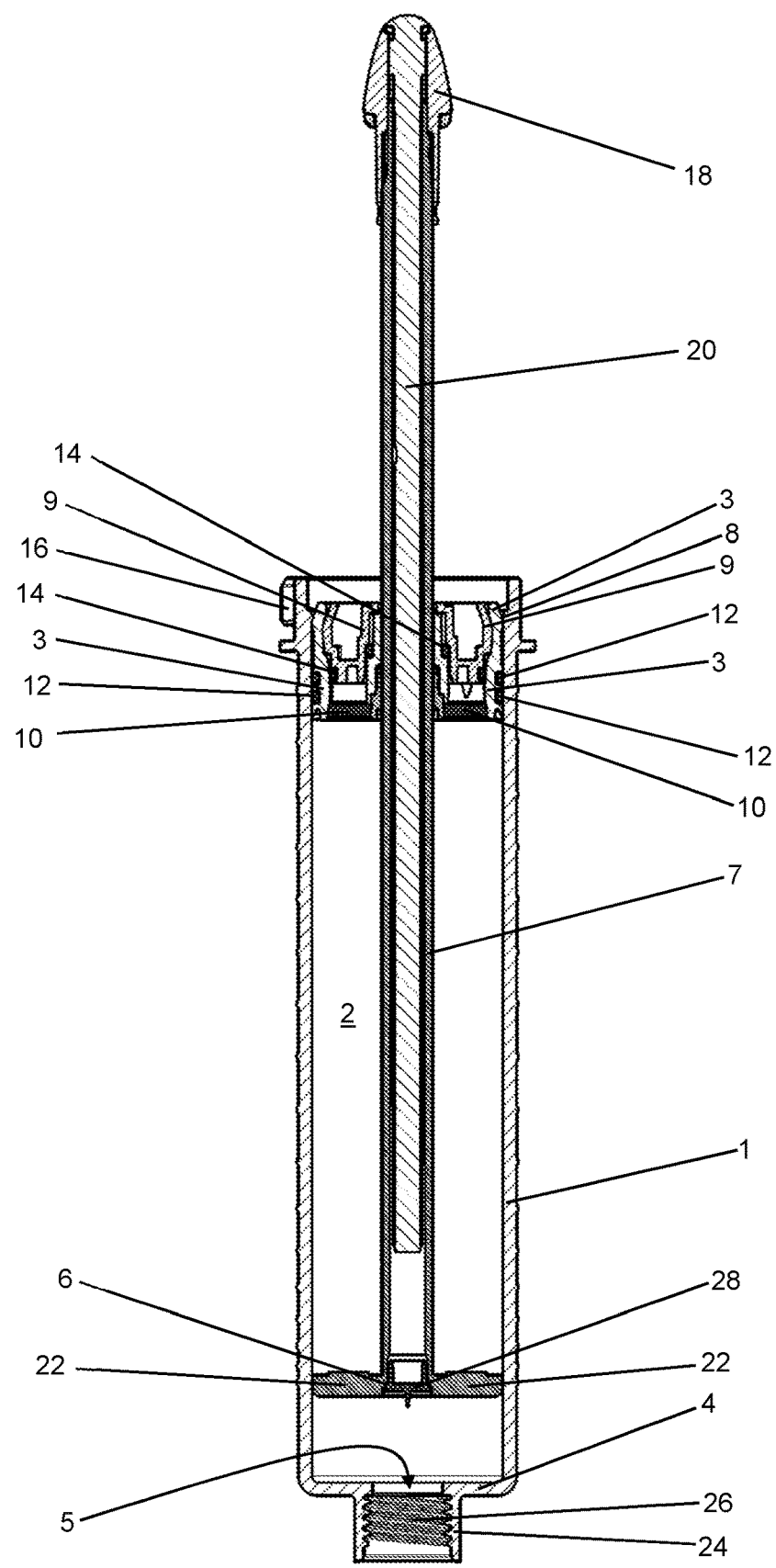
FIG. 2 illustrates a schematic perspective cross-sectional view of the bone cement applicator according to FIG. 1 with a delivery plunger which is locked in place.
Figure 3:
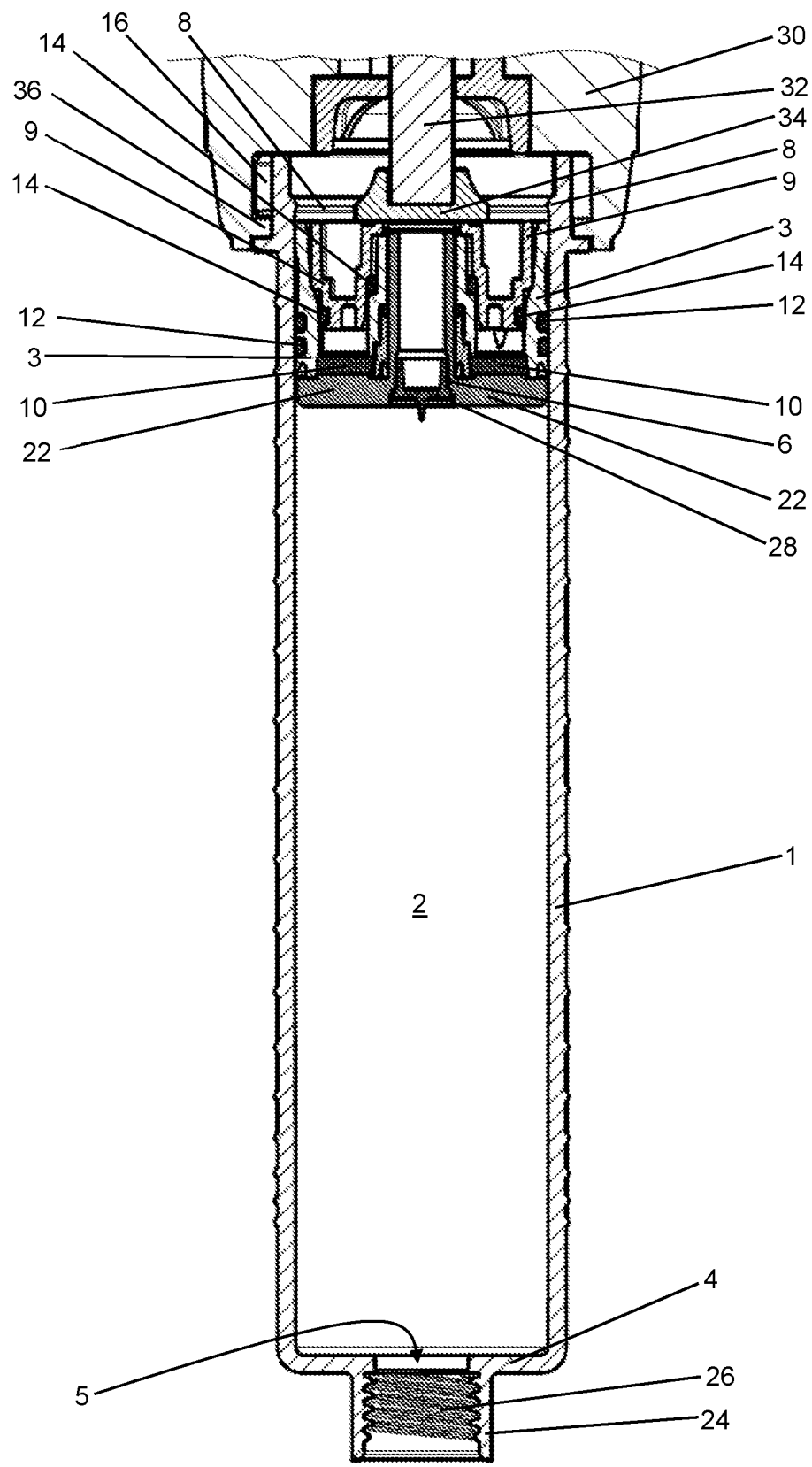
FIG. 3 illustrates a schematic perspective cross-sectional view of the bone cement applicator according to FIGS. 1 and 2 during expulsion with an expulsion device.
Figure 4:
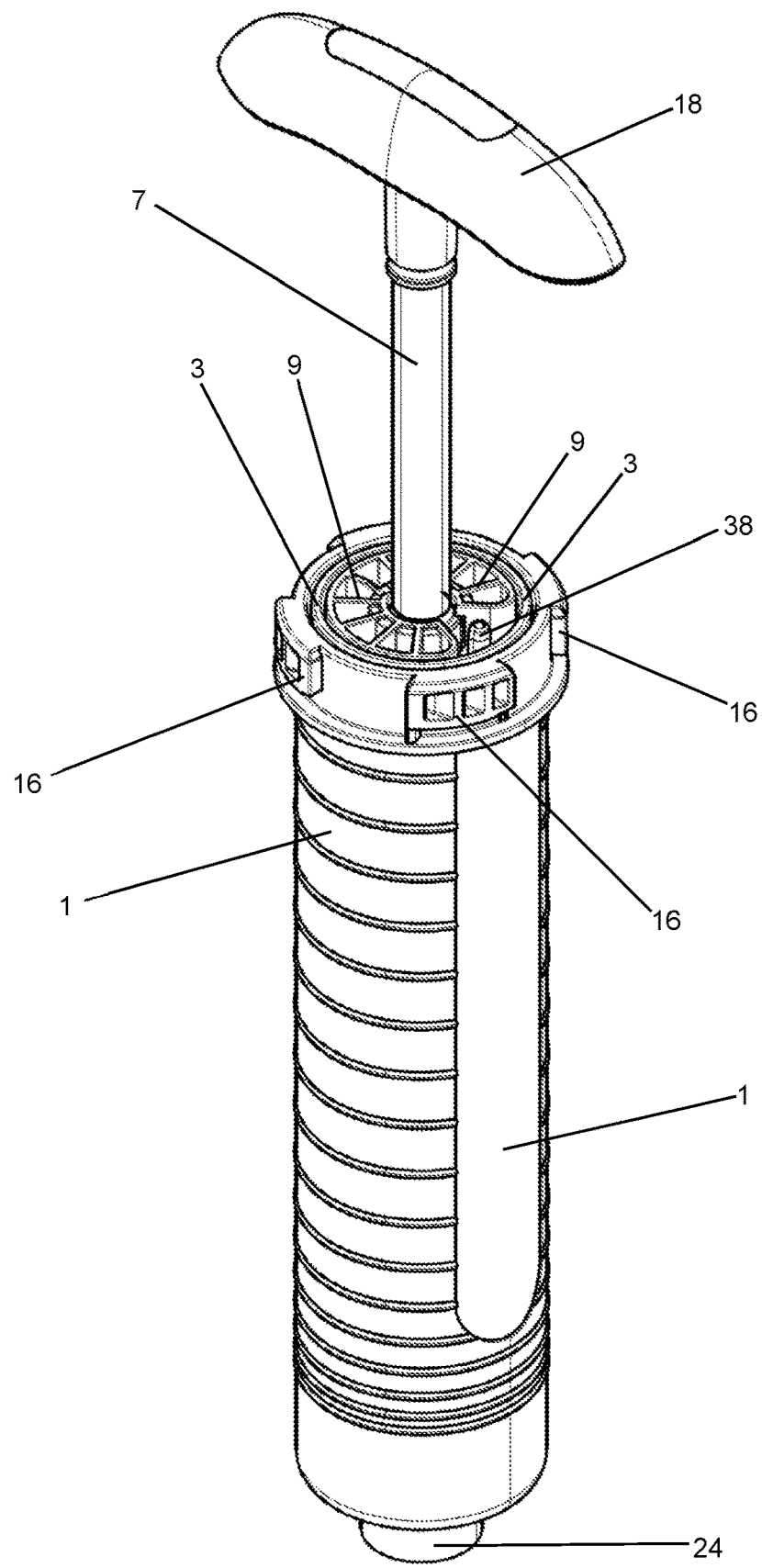
FIG. 4 illustrates a schematic perspective external view of the bone cement applicator according to FIGS. 1 to 3.

An expulsion device 30, the front part of which is shown in FIG. 3, may be used to release the clamping effect of the delivery plunger 3 with the clamping element 8 (see FIGS. 2, 5 and 8). Such expulsion devices 30 are well known from the prior art and are therefore not described in detail here. The expulsion device 30 may have an axially advanceable pushrod 32. At the tip of the pushrod 32 may be arranged a disk 34 with which the delivery plunger 3 is advanceable in the cartridge 1 axially in the direction of the cartridge head 4. The expulsion device 30 may be fastened via mating fastening means 36 to the fastening means 16 of the cartridge 1, for example in the manner of a bayonet closure. The expulsion device 30 is capable not only of releasing the clamping effect (see FIGS. 2, 5 and 8) but also of driving the delivery plunger 3 further in the direction of the cartridge head 4 and so discharging the contents of the cartridge 1 (i.e. the bone cement) from the interior of the cartridge 1 through the delivery opening 5. The expulsion device 30 may be driven manually in the manner of a cartridge gun or also using gas pressure or electrically.

A vacuum port 38 may be arranged on the delivery plunger 3 or the sealing plunger 9 for evacuating the interior 2 of the cartridge 1. Gas may be evacuated from the interior 2 of the cartridge 1 through the vacuum port 38 when the sealing plunger 9 seals the passage through the delivery plunger 3.

A central region of the delivery plunger 3 may be in the form of a sleeve 40 for guiding the mixing rod 7. At its connection to the inner wall of the cartridge 1 and/or to the mixing rod 7, the delivery plunger 3 may have wiper lips 42 which are capable of preventing bone cement from penetrating and escaping between the delivery plunger 3 and the inner wall of the cartridge 1 and between the delivery plunger 3 and the mixing rod 7.

When clamping the delivery plunger 3 with the clamping element 8, the clamping element 8 may press on a cylindrical outer circumferential surface 44 of the delivery plunger 3. The circumferential clamping element 8 may here radially compress the delivery plunger 3. The delivery plunger 3 may here be resiliently deformed by the clamping element 8, so bringing about the clamping effect and thus locking the delivery plunger. When the clamping effect is released with the expulsion device 30, the clamping effect may be released and the resilient deformation of the delivery plunger 3 may be reversed by renewed relaxation of the delivery plunger 3 or of the resiliently deformed regions of the delivery plunger 3, namely the circumferential surface 44 (see FIGS. 3 and 9).

The sleeve 40 may be connected via struts 46 to the outer regions of the delivery plunger 3 including the circumferential surface 44 of the delivery plunger 3. The passage for evacuation through the delivery plunger 3 may be formed between the struts 46. The porous filter 10 may be formed as an annular disk and rest on the struts 46. In order to prevent the porous filter 10 from falling out, the delivery plunger 3 may have an insert sleeve 48 with which the porous filter 10 is secured and through which the mixing rod 7 is guided.

The first exemplary bone cement applicator may be used as follows according to one embodiment. A cement powder may be present in the interior 2 of the cartridge 1 or is introduced into the interior 2. The delivery opening 5 is in one embodiment closed with a closure. The monomer liquid may then be added. The sealing plunger 9 may be inserted into the delivery plunger 3 for sealing. The delivery plunger 3 may be pushed into the cartridge 1 to such an extent that the clamping element 8 resiliently deforms the delivery plunger 3 at the circumferential surface 44 and so clamps the delivery plunger 3 in place. A vacuum can be generated in the interior 2 of the cartridge 1 via the vacuum port 38. The cement powder may be mixed with the monomer liquid by moving the mixing member 6 in the interior 2. The delivery plunger 3 does not here move with the mixing rod 7 since it is locked by clamping with the clamping element 8. The mixing member 6 may be drawn with the mixing rod 7 to the locked delivery plunger 3 and the mixing rod 7 can be broken off.

The bone cement applicator can then be inserted into the expulsion device 30. The delivery plunger 3 can be driven by advancing the pushrod 32. The clamping effect may here firstly be released and thus the delivery plunger 3 released from the clamping element 8. The closure may be removed from the delivery opening 5 and a delivery pipe may be fastened to the internal thread 26. By advancing the delivery plunger 3 further in the interior 2 of the cartridge 1 in the direction of the cartridge head 4, the bone cement can be pressed out of the delivery opening 5, where the bone cement paste can be expelled through the delivery pipe.

Figure 10:
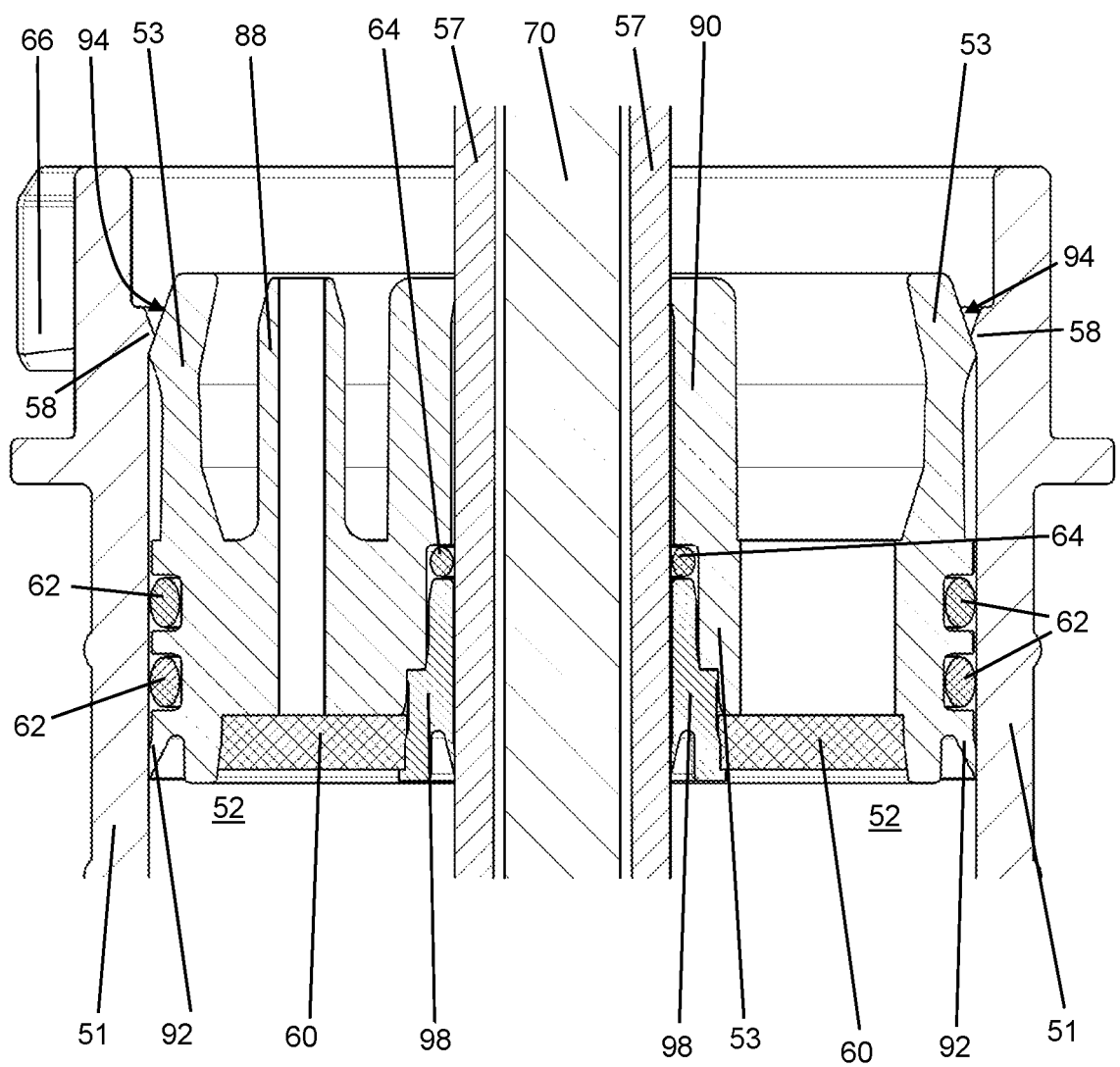
FIG. 10 illustrates a portion of a schematic cross-sectional view of a second exemplary bone cement applicator according to one embodiment for mixing and delivering a bone cement with a locked delivery plunger similar to FIG. 8.

FIG. 10 illustrates a portion of a second bone cement applicator according to one embodiment as a cross-sectional view. In the figure, the front side of the bone cement applicator is arranged at the bottom and the back side of the bone cement applicator at the top. The second bone cement applicator according to one embodiment is similar to the first according to FIGS. 1 to 9 with the exception of the one-part structure of the delivery plunger 53.

According to the second exemplary embodiment of the present embodiment, the bone cement applicator may have a tubular cartridge 51 of a plastics material with a cylindrical interior 52. A delivery plunger 53 mounted so as to be movable in an axial direction may be arranged in the cylindrical interior 52 of the cartridge 51. The cylindrical interior 52 may be closed by a cartridge head at a front side of the cartridge (not visible in FIG. 10). A delivery opening may be arranged in the cartridge head, through which opening a bone cement (not shown in FIG. 10), which may be present or mixed in the cylindrical interior 52 of the cartridge 51, may be discharged from the interior 52 with the delivery plunger 53. The delivery opening may be closable or closed. A cement powder (not shown) as parent component of the bone cement to be produced may be arranged in the cylindrical interior 52 of the cartridge 51. A monomer liquid (not shown) as second parent component can be added to the cement powder in the cylindrical interior 52 in order to mix the bone cement in the interior.

A mixing member (not visible in FIG. 10, but similar to the first exemplary embodiment) may be movably arranged in the cylindrical interior 52 for intermixing the contents of the interior 52. The mixing member may be moved axially with a mixing rod 57 in the cylindrical interior 52 and rotated about the axis of the mixing rod 57. The mixing rod 57 may be guided through a leadthrough in the delivery plunger 53 into the interior 52 of the cartridge 51.

A projecting rail as clamping element 58 for clamping the delivery plunger 53 in place may be arranged on the inner wall of the cartridge 51 in the region of the rear end of the cartridge 51 (at the top in FIG. 10). When the delivery plunger 53 is pressed into the rear end of the cartridge 51, the clamping element 58 may exert radial pressure onto the delivery plunger 53. The delivery plunger 53 can be resiliently deformed by the radial pressure. The resilient deformation of the delivery plunger 53 may clamp the delivery plunger 53 at the level of the clamping element 58.

A porous filter 60 which is permeable to gases but impermeable to the cement powder may be arranged in a passage through the delivery plunger 53. The interior 52 of the cartridge 51 and the contents thereof may be sterilized with the assistance of a sterilizing gas such as ethylene oxide through the passage in the delivery plunger 53 and optionally through the porous filter 60 and the interior 52 of the cartridge 51 evacuated so that the bone cement can be mixed under a vacuum.

In order to enable evacuation of the interior 52, two circumferential seals 62 of rubber may be arranged on the outer wall of the delivery plunger 53, said seals sealing the delivery plunger 53 relative to the inner wall of the cartridge 51 and thus the cylindrical interior 52. The mixing rod 57 may likewise be sealed relative to the delivery plunger 53 with a circumferential seal 64.

A plurality of fastening means 66 to which an expulsion device may be fastened (not shown but similar to FIG. 3) may be arranged externally on the back side of the cartridge 51.

The mixing member can be moved with the mixing rod 57 in the interior 52 of the cartridge 51. A core 70 which mechanically stabilizes the mixing rod 57 may be arranged in the interior of the mixing rod 57. The mixing rod 57 may be movably mounted in a leadthrough through the delivery plunger 53. The mixing rod 57 may be moved axially through the leadthrough through the delivery plunger 53 and in one embodiment also be rotated in the leadthrough. If the mixing member is rigidly connected to the mixing rod 57, the mixing member may accordingly be moved axially and in one embodiment also rotated in the interior 52 of the cartridge 51. This means the contents of the cartridge 51 are manually mixable with the mixing member.

An expulsion device similar to FIG. 3 may be used for releasing the clamping effect of the delivery plunger 53 with the clamping element 58 (see FIG. 10). The expulsion device 30 is capable not only of releasing the clamping effect (see FIG. 10) but also of driving the delivery plunger 53 further in the direction of the cartridge head and so discharging the contents of the cartridge 51 (i.e. the bone cement) from the interior of the cartridge 51 through the delivery opening.

A vacuum port 88, which is connected with the passage through the delivery plunger 53, may be arranged on the delivery plunger 53 for evacuating the interior 52 of the cartridge 51. Gas may be evacuated from the interior 52 of the cartridge 51 through the vacuum port 88.

A central region of the delivery plunger 53 may be in the form of a sleeve 90 for guiding the mixing rod 57. At its connection to the inner wall of the cartridge 51 and/or to the mixing rod 57, the delivery plunger 53 may have wiper lips 92 which are capable of preventing bone cement from penetrating and escaping between the delivery plunger 53 and the inner wall of the cartridge 51 and between the delivery plunger 53 and the mixing rod 57.

When clamping the delivery plunger 53 with the clamping element 58, the clamping element 58 may press on a cylindrical outer circumferential surface 94 of the delivery plunger 53. The circumferential clamping element 58 may here radially compress the delivery plunger 53. The delivery plunger 53 may here be resiliently deformed by the clamping element 58, so bringing about the clamping effect and thus locking the delivery plunger. When the clamping effect is released with the expulsion device, the clamping effect may be released and the resilient deformation of the delivery plunger 53 may be reversed by renewed relaxation of the delivery plunger 53 or of the resiliently deformed regions of the delivery plunger 53, namely the circumferential surface 94.

In order to prevent the porous filter 60 from falling out, the delivery plunger 53 may have an insert sleeve 98 with which the porous filter 60 is secured and through which the mixing rod 57 is guided.

The second exemplary bone cement applicator may be used as follows according to one embodiment. A cement powder may be present in the interior 52 of the cartridge 51 or is introduced into the interior 52. The delivery opening is in one embodiment closed with a closure. The monomer liquid may then be added. The delivery plunger 53 may be pushed into the cartridge 51 to such an extent that the clamping element 58 resiliently deforms the delivery plunger 53 at the circumferential surface 94 and thereby clamps the delivery plunger 53 in place. A vacuum can be generated in the interior 52 of the cartridge 51 via the vacuum port 88. The cement powder may be mixed with the monomer liquid by moving the mixing member in the interior 52. The delivery plunger 53 does not here move with the mixing rod 57 since it is locked by clamping with the clamping element 58. The mixing member may be drawn with the mixing rod 57 to the locked delivery plunger 53 and the mixing rod 57 can be broken off.

The bone cement applicator can then be inserted into an expulsion device. On driving the delivery plunger 53, the clamping effect may firstly be released and thus the delivery plunger 53 released from the clamping element 58. The closure may be removed from the delivery opening and a delivery pipe may be fastened to the cartridge 51. By advancing the delivery plunger 53 further in the interior 52 of the cartridge 51, the bone cement can be pressed out of the delivery opening, where the bone cement paste can be expelled through the delivery pipe.

Figure 11:
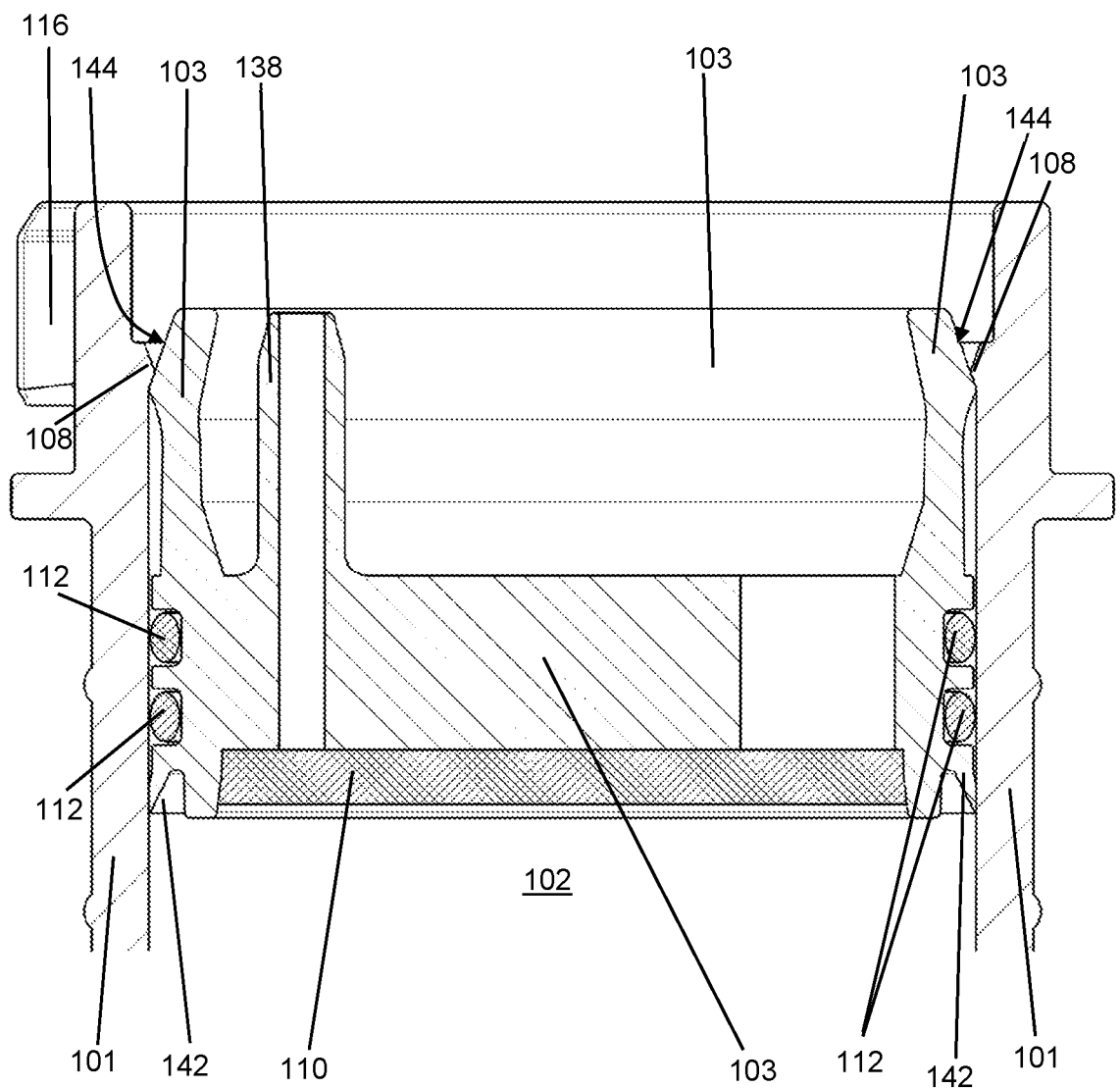
FIG. 11 illustrates a portion of a schematic cross-sectional view of a third exemplary bone cement applicator according to one embodiment for mixing and delivering a bone cement with a locked delivery plunger similar to FIG. 8.
Figure 12:
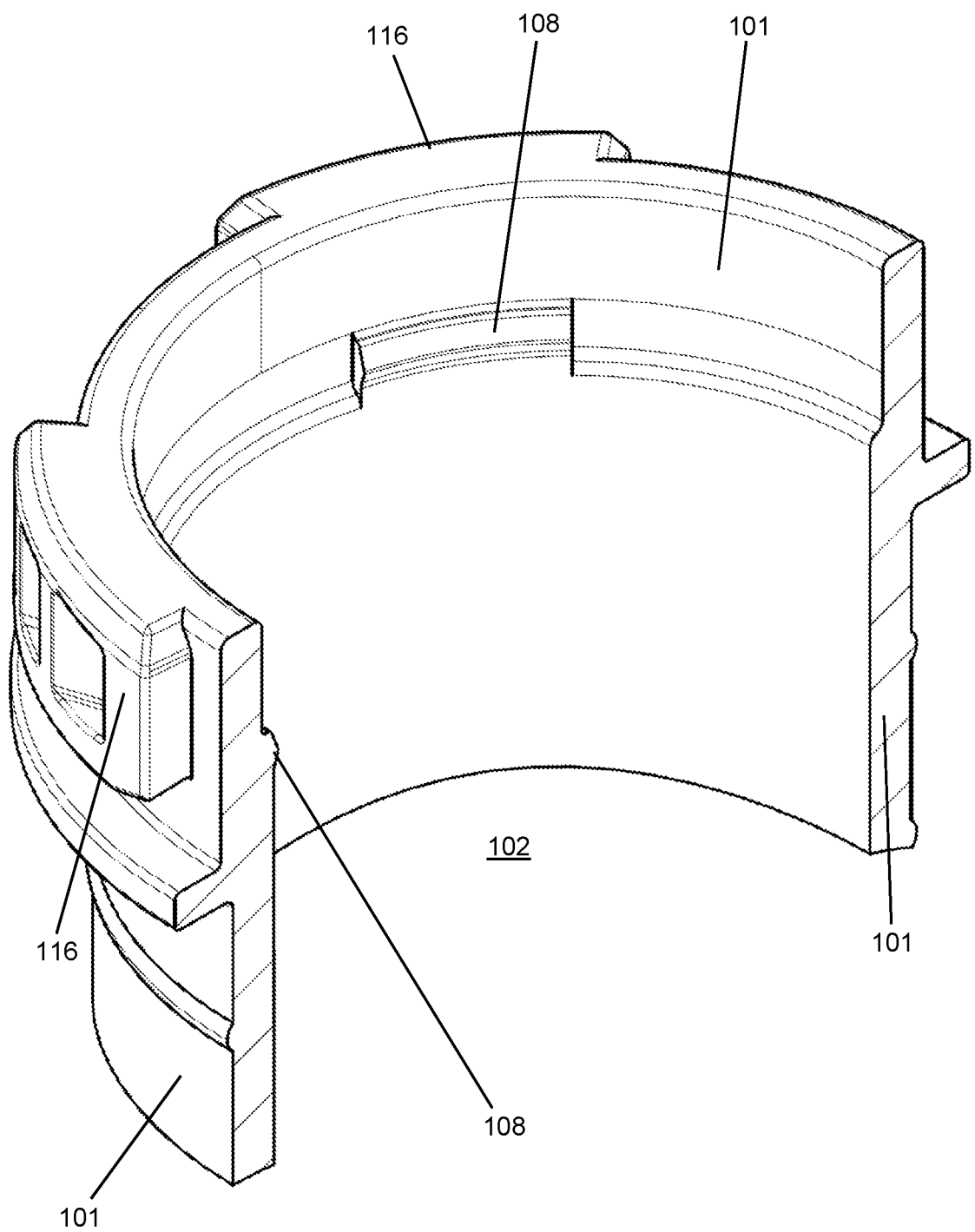
FIG. 12 illustrates the cartridge of the third exemplary bone cement applicator according to FIG. 11 as an individual schematic perspective detail and cross-sectional view.

FIGS. 11 and 12 show a portion of a third bone cement applicator according to one embodiment as a cross-sectional view. In the figures, the front side of the bone cement applicator is arranged at the bottom and the back side of the bone cement applicator at the top. The third bone cement applicator according to one embodiment is similar to the first according to FIGS. 1 to 9 with the exception of the one-part structure of the delivery plunger 103 and the absence of the leadthrough for the mixing rod.

According to the third exemplary embodiment of the present embodiment, the bone cement applicator may have a tubular cartridge 101 of a plastics material with a cylindrical interior 102. A delivery plunger 103 mounted so as to be movable in an axial direction may be arranged in the cylindrical interior 102 of the cartridge 101. The cylindrical interior 102 may be closed by a cartridge head at a front side of the cartridge (not visible in FIGS. 11 and 12). A delivery opening may be arranged in the cartridge head, through which opening a bone cement (not shown in FIGS. 11 and 12), which may be present or mixed in the cylindrical interior 102 of the cartridge 101, may be discharged from the interior 102 with the delivery plunger 103. The delivery opening may be closable or closed. A cement powder (not shown) as parent component of the bone cement to be produced may be arranged in the cylindrical interior 102 of the cartridge 101. A monomer liquid (not shown) as second parent component can be added to the cement powder in the cylindrical interior 102 in order to mix the bone cement in the interior.

A mixing member (not visible in FIGS. 11 and 12, but similar to the first exemplary embodiment) may be movably arranged in the cylindrical interior 102 for intermixing the contents of the interior 102. The mixing member may be moved axially with a mixing rod (not visible in FIGS. 11 and 12) in the cylindrical interior 102 and rotated about the axis of the mixing rod. The mixing rod may be guided through the delivery opening in the cartridge head into the interior 102 of the cartridge 101.

A projecting rail as clamping element 108 for clamping the delivery plunger 103 in place may be arranged on the inner wall of the cartridge 101 in the region of the rear end of the cartridge 101 (at the top in the figures). When the delivery plunger 103 is pressed into the rear end of the cartridge 101, the clamping element 108 may exert radial pressure onto the delivery plunger 103. The delivery plunger 103 can be resiliently deformed by the radial pressure. The resilient deformation of the delivery plunger 103 may clamp the delivery plunger 103 at the level of the clamping element 108. As is apparent from FIG. 12, the clamping element may be formed as a discontinuous rail with interruptions in order to increase the clamping action due to the smaller contact area.

A porous filter 110 which is permeable to gases but impermeable to the cement powder may be arranged in a passage through the delivery plunger 103. The interior 102 of the cartridge 101 and the contents thereof may be sterilized with the assistance of a sterilizing gas such as ethylene oxide through the passage in the delivery plunger 103 and optionally through the porous filter 110 and the interior 102 of the cartridge 101 evacuated so that the bone cement can be mixed under a vacuum.

In order to enable evacuation of the interior 102, two circumferential seals 112 of rubber may be arranged on the outer wall of the delivery plunger 103, said seals sealing the delivery plunger 103 relative to the inner wall of the cartridge 101 and thus the cylindrical interior 102.

A plurality of fastening means 116 to which an expulsion device may be fastened (not shown but similar to FIG. 3) may be arranged externally on the back side of the cartridge 101.

The mixing member can be moved with the mixing rod in the interior 102 of the cartridge 101. The mixing rod may be movably mounted in a leadthrough through the cartridge head. The mixing rod may be moved axially through the leadthrough in the cartridge head and in one embodiment also be rotated in the leadthrough. If the mixing member is rigidly connected to the mixing rod, the mixing member may accordingly be moved axially and in one embodiment also rotated in the interior 102 of the cartridge 101. This means the contents of the cartridge 101 are manually mixable with the mixing member.

An expulsion device similar to FIG. 3 may be used for releasing the clamping effect of the delivery plunger 103 with the clamping element 108 (see FIG. 11). The expulsion device 30 is capable not only of releasing the clamping effect (see FIG. 11) but also of driving the delivery plunger 103 further in the direction of the cartridge head and so discharging the contents of the cartridge 101 (i.e. the bone cement) from the interior of the cartridge 101 through the delivery opening.

A vacuum port 138, which is connected with the passage through the delivery plunger 103, may be arranged on the delivery plunger 103 for evacuating the interior 102 of the cartridge 101. Gas may be evacuated from the interior 102 of the cartridge 101 through the vacuum port 138.

At its connection to the inner wall of the cartridge 101, the delivery plunger 103 may have wiper lips 142 which are capable of preventing bone cement from penetrating and escaping between the delivery plunger 103 and the inner wall of the cartridge 101.

When clamping the delivery plunger 103 with the clamping element 108, the clamping element 108 may press on a cylindrical outer circumferential surface 144 of the delivery plunger 103. The circumferential clamping element 108 may here radially compress the delivery plunger 103. The delivery plunger 103 may here be resiliently deformed by the clamping element 108, so bringing about the clamping effect and thus locking the delivery plunger. When the clamping effect is released with the expulsion device, the clamping effect may be released and the resilient deformation of the delivery plunger 103 may be reversed by renewed relaxation of the delivery plunger 103 or of the resiliently deformed regions of the delivery plunger 103, namely the circumferential surface 144.

The third exemplary bone cement applicator may be used as follows according to one embodiment. A cement powder may be present in the interior 102 of the cartridge 101 or is introduced into the interior 102. The delivery opening is in one embodiment closed with a closure. The monomer liquid may then be added. The delivery plunger 103 may be pushed into the cartridge 101 to such an extent that the clamping element 108 resiliently deforms the delivery plunger 103 at the circumferential surface 94 and so clamps the delivery plunger 103 in place. A vacuum can be generated in the interior 102 of the cartridge 101 via the vacuum port 138. The cement powder may be mixed with the monomer liquid by moving the mixing member in the interior 102. The delivery plunger 103 does not here move since it is locked by clamping with the clamping element 108. The mixing member may be drawn with the mixing rod to the cartridge head and the mixing rod can be drawn out, so opening the delivery opening.

The bone cement applicator can then be inserted into an expulsion device. On driving the delivery plunger 103, the clamping effect may firstly be released and thus the delivery plunger 103 released from the clamping element 108. The closure may be removed from the delivery opening and a delivery pipe may be fastened to the cartridge 101. By advancing the delivery plunger 103 further in the interior 102 of the cartridge 101, the bone cement can be pressed out of the delivery opening, where the bone cement paste can be expelled through the delivery pipe.

Figure 13:
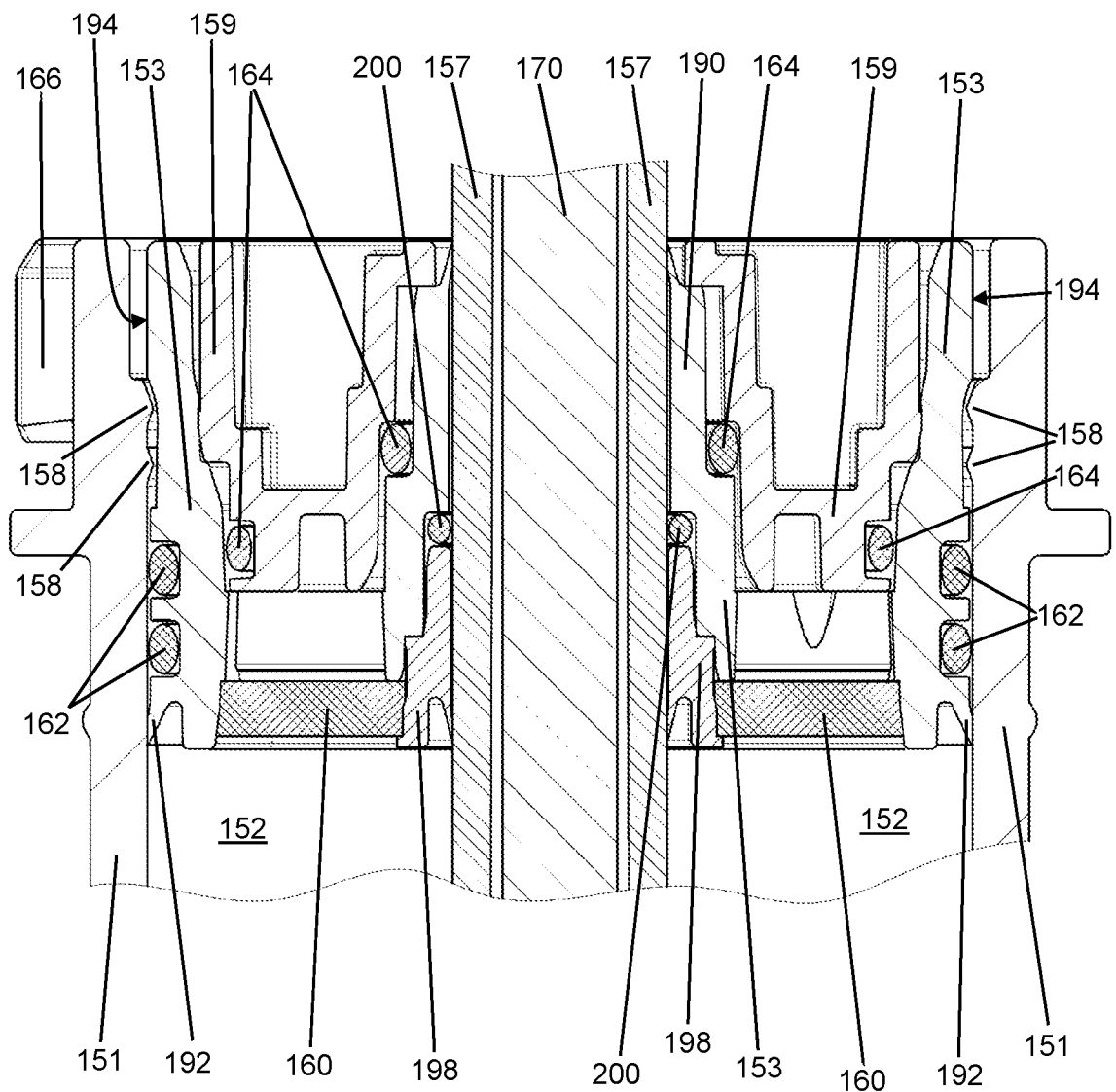
FIG. 13 illustrates a portion of a schematic cross-sectional view of a fourth exemplary bone cement applicator according to one embodiment for mixing and delivering a bone cement with an unlocked delivery plunger similar to FIG. 7.

FIG. 13 illustrates a portion of a fourth bone cement applicator according to one embodiment as a cross-sectional view. In the figure, the front side of the bone cement applicator is arranged at the bottom and the back side of the bone cement applicator at the top. The fourth bone cement applicator according to one embodiment is similar to the first according to FIGS. 1 to 9 with the exception of the dual clamping elements 158. In contrast with the first exemplary embodiment, two circumferential projecting rails are provided as clamping elements 158.

According to the fourth exemplary embodiment, the bone cement applicator may have a tubular cartridge 151 of a plastics material with a cylindrical interior 152. A delivery plunger 153 mounted so as to be movable in an axial direction may be arranged in the cylindrical interior 152 of the cartridge 151. The cylindrical interior 152 may be closed by a cartridge head at a front side of the cartridge (not visible in FIG. 13). A delivery opening may be arranged in the cartridge head, through which opening a bone cement (not shown in FIG. 13), which may be present or mixed in the cylindrical interior 152 of the cartridge 151, may be discharged from the interior 152 with the delivery plunger 153. The delivery opening may be closable or closed. A cement powder (not shown) as parent component of the bone cement to be produced may be arranged in the cylindrical interior 152 of the cartridge 151. A monomer liquid (not shown) as second parent component can be added to the cement powder in the cylindrical interior 152 in order to mix the bone cement in the interior.

A mixing member (not visible in FIG. 13, but similar to the first exemplary embodiment) may be movably arranged in the cylindrical interior 152 for intermixing the contents of the interior 152. The mixing member may be moved axially with a mixing rod 157 in the cylindrical interior 152 and rotated about the axis of the mixing rod 157. The mixing rod 157 may be guided through a leadthrough in the delivery plunger 153 into the interior 152 of the cartridge 151.

Two projecting circumferential rails as clamping elements 158 for clamping the delivery plunger 153 in place may be arranged on the inner wall of the cartridge 151 in the region of the rear end of the cartridge 151 (at the top in FIG. 13). When the delivery plunger 153 is pressed into the rear end of the cartridge 151, the clamping elements 158 may exert radial pressure onto the delivery plunger 153. The delivery plunger 153 can be resiliently deformed by the radial pressure. The resilient deformation of the delivery plunger 153 may clamp the delivery plunger 153 at the level of the clamping element 158.

In the back side of the delivery plunger 153, a sealing plunger 159 may be arranged with which a passage through the delivery plunger 153 may be sealed. A porous filter 160 which is permeable to gases but impermeable to the cement powder may be arranged in the passage through the delivery plunger 153. The interior 152 of the cartridge 151 and the contents thereof may be sterilized with the assistance of a sterilizing gas such as ethylene oxide through the passage in the delivery plunger 153 and optionally through the porous filter 160. The sealing plunger 159 may then be inserted to seal the passage. When the passage is sealed, the interior 152 of the cartridge 151 can be evacuated in order to permit mixing of the bone cement under a vacuum.

In order to enable evacuation of the interior 152, two circumferential seals 162 of rubber may be arranged on the outer wall of the delivery plunger 153, said seals sealing the delivery plunger 153 relative to the inner wall of the cartridge 151 and thus the cylindrical interior 152. The sealing plunger 159 may likewise be sealed relative to the delivery plunger 153 with a circumferential seal 164. The delivery plunger 153 may further be sealed relative to the mixing rod 157 with a circumferential seal 200.

A plurality of fastening means 166 to which an expulsion device may be fastened (not shown but similar to FIG. 3) may be arranged externally on the back side of the cartridge 151.

The mixing member can be moved with the mixing rod 157 in the interior 152 of the cartridge 151. A core 170 which mechanically stabilizes the mixing rod 157 may be arranged in the interior of the mixing rod 157. The mixing rod 157 may be movably mounted in a leadthrough through the delivery plunger 153. The mixing rod 157 may be moved axially through the leadthrough through the delivery plunger 153 and in one embodiment also be rotated in the leadthrough. If the mixing member is rigidly connected to the mixing rod 157, the mixing member may accordingly be moved axially and in one embodiment also rotated in the interior 152 of the cartridge 151. This means the contents of the cartridge 151 are manually mixable with the mixing member.

An expulsion device similar to FIG. 3 may be used for releasing the clamping effect of the delivery plunger 153 with the clamping element 158. The expulsion device 30 is capable not only of releasing the clamping effect but also of driving the delivery plunger 153 further in the direction of the cartridge head and so discharging the contents of the cartridge 151 (i.e. the bone cement) from the interior of the cartridge 151 through the delivery opening.

A vacuum port (not shown) may be arranged on the delivery plunger 153 for evacuating the interior 152 of the cartridge 151. Gas may be evacuated from the interior 152 of the cartridge 151 through the vacuum port.

A central region of the delivery plunger 153 may be in the form of a sleeve 190 for guiding the mixing rod 157. At its connection to the inner wall of the cartridge 151 and/or to the mixing rod 157, the delivery plunger 153 may have wiper lips 192 which are capable of preventing bone cement from penetrating and escaping between the delivery plunger 153 and the inner wall of the cartridge 151 and between the delivery plunger 153 and the mixing rod 157.

When clamping the delivery plunger 153 with the clamping element 158, the clamping element 158 may press on a cylindrical outer circumferential surface 194 of the delivery plunger 153. The circumferential clamping element 158 may here radially compress the delivery plunger 153. The delivery plunger 153 may here be resiliently deformed by the clamping element 158, so bringing about the clamping effect and thus locking the delivery plunger. When the clamping effect is released with the expulsion device, the clamping effect may be released and the resilient deformation of the delivery plunger 153 may be reversed by renewed relaxation of the delivery plunger 153 or of the resiliently deformed regions of the delivery plunger 153, namely the circumferential surface 194.

In order to prevent the porous filter 160 from falling out, the delivery plunger 153 may have an insert sleeve 198 with which the porous filter 160 is secured and through which the mixing rod 157 is guided.

The fourth exemplary bone cement applicator may be used as follows according to one embodiment. A cement powder may be present in the interior 152 of the cartridge 151 or is introduced into the interior 152. The delivery opening is in one embodiment closed with a closure. The monomer liquid may then be added. The delivery plunger 153 may be pushed into the cartridge 151 to such an extent that the clamping elements 158 resiliently deform the delivery plunger 153 at the circumferential surface 194 and so clamp the delivery plunger 153 in place. A vacuum can be generated in the interior 152 of the cartridge 151 via the vacuum port. The cement powder may be mixed with the monomer liquid by moving the mixing member in the interior 152. The delivery plunger 153 does not here move with the mixing rod 157 since it is locked by clamping with the clamping element 158. The mixing member may be drawn with the mixing rod 157 to the locked delivery plunger 153 and the mixing rod 157 can be broken off.

The bone cement applicator can then be inserted into an expulsion device. On driving the delivery plunger 153, the clamping effect may firstly be released and thus the delivery plunger 153 released from the clamping elements 158. The closure may be removed from the delivery opening and a delivery pipe may be fastened to the cartridge 151. By advancing the delivery plunger 153 further in the interior 152 of the cartridge 151, the bone cement can be pressed out of the delivery opening, where the bone cement paste can be expelled through the delivery pipe.

The features of embodiments disclosed in the above description, as well as in the claims, figures and exemplary embodiments, may be essential both individually and in any desired combination to realization of its various embodiments.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:

1. A bone cement applicator for providing a polymethyl methacrylate bone cement, the bone cement applicator comprising:

a cartridge with a cylindrical interior;

a cartridge head with a delivery opening for discharging the bone cement, wherein the cartridge head closes the cylindrical interior of the cartridge at a front side of the cartridge except for the delivery opening;

a mixing member movably arranged in the cylindrical interior of the cartridge and is movable in the interior with a mixing rod guided into the interior;

a delivery plunger arranged in the cartridge and is mounted slidably in the direction of the delivery opening in the cylindrical interior of the cartridge, wherein the delivery plunger has an outer cylindrical circumferential surface and wherein the delivery plunger rests with its outer cylindrical circumferential surface against an inner wall of the cartridge, the inner wall defining the cylindrical interior; and at least one clamping element arranged in the region of a back side, opposite the front side of the cartridge, of the cylindrical interior on the inner wall of the cartridge, the inner wall defining the cylindrical interior, wherein the at least one clamping element projects out from the inner wall of the cartridge in the direction of the cylindrical interior;

wherein the cylindrical circumferential surface of the delivery plunger is at least in places resiliently deformed by the at least one clamping element in the direction of a central cylinder axis of the cylindrical interior, such that the delivery plunger is clampable in place with the at least one clamping element on the back side of the cartridge.

2. The bone cement applicator according to claim 1, wherein the at least one clamping element is formed as a part of the cartridge.

3. The bone cement applicator according to claim 1, wherein the delivery opening is closed or closable in the cartridge head with a releasable closure, wherein a thread is arranged on the cartridge head, into or onto which the closure is screwed or screwable with a mating thread which fits the thread, in order to close the delivery opening.

4. The bone cement applicator according to claim 1, wherein an external diameter of the delivery plunger is the same size as or smaller than the internal diameter of the cylindrical interior of the cartridge, wherein at least one circumferential seal and/or a circumferential wiper lip is arranged on the outer circumference of the delivery plunger.

5. The bone cement applicator according to claim 1, wherein the internal diameter of the cylindrical interior of the cartridge is reduced in the region of the at least one clamping element by the at least one clamping element, wherein the internal diameter is reduced to such an extent that the delivery plunger has an external diameter larger than the internal diameter reduced by the at least one clamping element.

6. The bone cement applicator according to claim 1, wherein the at least one clamping element is a circumferential, closed projecting rail or portions of a circumferential rail or at least two circumferential, closed rails spaced apart in an axial direction or at least two portions of a circumferential rail spaced apart in an axial direction.

7. The bone cement applicator according to claim 1, wherein the at least one clamping element has a chamfer on a front side of the at least one clamping element, said front side facing towards the front side of the cartridge, and a chamfer on a back side of the at least one clamping element, said back side facing towards the back side of the cartridge.

8. The bone cement applicator according to claim 1, wherein two or more clamping elements are arranged, axially spaced apart with regard to the longitudinal cylinder axis, on the inner wall defining the cylindrical interior.

9. The bone cement applicator according to claim 1, wherein an outer wall of the delivery plunger, the outer wall facing towards the inner wall of the cylindrical interior, has an axial extent which is at least the same size as the axial extent of the at least one clamping element, wherein the axial extent of the outer wall of the delivery plunger is at least twice the size of the axial extent of the at least one clamping element.

10. The bone cement applicator according to claim 1, wherein an outer wall of the delivery plunger, said outer wall facing towards the inner wall of the cylindrical interior, is formed as a hollow cylinder.

11. The bone cement applicator according to claim 1, wherein the delivery plunger clamped in place by the at least one clamping element is releasable by the action of a force directed along the cylinder axis of the cartridge and is pressable in the direction of the front side of the cartridge.

12. The bone cement applicator according to claim 1, wherein the outer cylindrical circumferential surface of the delivery plunger consists of a thermoplastic, wherein the thermoplastic is selected from at least one of the plastics materials polyethylene, polypropylene, polyamide, polyethylene terephthalate and polybutylene terephthalate.

13. The bone cement applicator according to claim 1, wherein the bone cement applicator has a sealing plunger which is connectable to the delivery plunger, wherein the delivery plunger comprises the outer cylindrical circumferential surface and a passage which is permeable to gases but impermeable to the cement powder and wherein the passage in the delivery plunger is closable by the sealing plunger.

14. The bone cement applicator according to claim 13, wherein the passage in the delivery plunger is closable by the sealing plunger by inserting the sealing plunger into an opening of the delivery plunger, the opening being open in the direction of the back side of the cartridge, wherein the passage is arranged within the opening of the delivery plunger.

15. A method for producing a paste-like polymethyl methacrylate bone cement, wherein the bone cement paste is produced from a cement powder and a monomer liquid using a bone cement applicator according to claim 1, characterized by the following succession of steps:

A) introducing the cement powder and the monomer liquid into the cylindrical interior of the cartridge or the monomer liquid to the cement powder in the cylindrical interior of the cartridge,
B) closing the back side of the cartridge by pressing the delivery plunger into the cylindrical interior of the cartridge,
C) clamping the delivery plunger in a fixed place on the back side of the cartridge with the at least one clamping element,
D) mixing the bone cement in the cylindrical interior of the cartridge by moving the mixing member in the cylindrical interior of the cartridge,
E) pressing in the delivery plunger in the direction of the front side of the cartridge, wherein the clamping effect of the at least one clamping element is released, and
F) expelling the bone cement from the cartridge through the delivery opening by advancing the delivery plunger in the interior of the cartridge in the direction of the cartridge head.

16. The method according to claim 15, wherein the cement powder is introduced into the interior of the cartridge before the monomer liquid or is already present in the cylindrical interior of the cartridge.

17. The method according to claim 15, wherein on clamping the delivery plunger in place in step C), the delivery plunger is resiliently deformed in the direction of the cylinder axis of the cylindrical interior of the cartridge, wherein a tubular extension on the back side of the delivery plunger, the outer side of which is defined in part by the outer cylindrical circumferential surface of the delivery plunger, is pressed by the at least one clamping element in the direction of the cylinder axis of the cylindrical interior of the cartridge.

18. The method according to claim 15, wherein in step D), the mixing member is moved with the mixing rod and then drawn with the mixing rod against a front side of the delivery plunger, which front side faces towards the front side of the cartridge, and then the mixing rod is broken off.

19. The method according to claim 15, wherein before step E), the bone cement applicator is inserted into an expulsion device with an axially mobile and drivable ram, wherein in step E) and in step F) the delivery plunger is advanced with the ram.

20. The method according to claim 15, wherein the delivery opening is closed and is opened before step E) or F).

* * * * *